United States Patent
Katlinskaya et al.

(10) Patent No.: US 12,168,676 B2
(45) Date of Patent: Dec. 17, 2024

(54) MICROBIALLY DERIVED PEPTIDES AND PROTEINS FOR IMMUNOTHERAPY

(71) Applicant: Genevive, Inc., San Mateo, CA (US)

(72) Inventors: Yuliya Katlinskaya, Brisbane, CA (US); Helena Kiefel, Brisbane, CA (US); Kareem L. Graham, Brisbane, CA (US); Todd Z. DeSantis, Brisbane, CA (US); Sunit Jain, Brisbane, CA (US); Andrew W. Han, Brisbane, CA (US); Karim Dabbagh, Brisbane, CA (US)

(73) Assignee: Genevive, Inc., San Mateo, CA (US)

( * ) Notice: Subject to any disclaimer, the term of this patent is extended or adjusted under 35 U.S.C. 154(b) by 727 days.

(21) Appl. No.: 17/420,813

(22) PCT Filed: Jan. 6, 2020

(86) PCT No.: PCT/US2020/012431
§ 371 (c)(1),
(2) Date: Jul. 6, 2021

(87) PCT Pub. No.: WO2020/142786
PCT Pub. Date: Jul. 9, 2020

(65) Prior Publication Data
US 2022/0089653 A1 Mar. 24, 2022

Related U.S. Application Data

(60) Provisional application No. 62/788,950, filed on Jan. 6, 2019.

(51) Int. Cl.
| | |
|---|---|
| *C07K 14/195* | (2006.01) |
| *A61K 38/00* | (2006.01) |
| *A61P 35/00* | (2006.01) |
| *A61P 37/04* | (2006.01) |

(52) U.S. Cl.
CPC ............ *C07K 14/195* (2013.01); *A61P 35/00* (2018.01); *A61P 37/04* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 5,767,063 | A | 6/1998 | Lee et al. |
| 6,300,638 | B1 | 10/2001 | Groger et al. |
| 2006/0211639 | A1 | 9/2006 | Bratzler et al. |
| 2009/0067458 | A1 | 3/2009 | Ji et al. |
| 2010/0064393 | A1 | 3/2010 | Berka et al. |
| 2011/0169984 | A1 | 7/2011 | Noguchi |
| 2011/0213252 | A1 | 9/2011 | Fulghum |
| 2012/0117867 | A1 | 5/2012 | Hendriks et al. |
| 2016/0183775 | A1 | 6/2016 | Blanquart et al. |
| 2016/0279215 | A1 | 9/2016 | Mahr et al. |
| 2016/0331830 | A1 | 11/2016 | Franchini et al. |
| 2016/0339078 | A1 | 11/2016 | Hamill et al. |
| 2017/0078548 | A1 | 3/2017 | Blanquart |
| 2018/0310828 | A1 | 11/2018 | DiMaio |
| 2023/0272016 | A1 | 8/2023 | Hwang et al. |

FOREIGN PATENT DOCUMENTS

| | | |
|---|---|---|
| CN | 102451195 A | 5/2012 |
| SG | 139132 A1 | 2/2008 |
| WO | WO 2004/076615 | 9/2004 |
| WO | WO 2018/226690 | 12/2018 |
| WO | WO 2021/035983 | 12/2021 |
| WO | WO 2021/252289 | 12/2021 |

OTHER PUBLICATIONS

Akira et al., "Toll-like receptor signaling," Nat. Rev. Immunol., 2004, 4:499-511.

Bowie et al., "Deciphering the message in protein sequences: tolerance to amino acid substitutions," Science, 1990, 247:1306-1310.

Cristescu et al., "Pan-tumor genomic biomarkers for PD-1 checkpoint blockade-based immunotherapy," Science. 2018; 362(6411).

Curtsinger et al., "Signal 3 Determines Tolerance versus Full Activation of Naïve CD8 T Cells: Dissociating Proliferation and Development ofEffector Function," 2003, J. Exp. Med. 197:1141-51.

Dustin et al., "The immunological synapse and the actin cytoskeleton: molecular hardware for T cell signaling, "Nat. Immunol., 2000, 1:23-9.

Eisenhauer et al., "New response evaluation criteria in solid tumors: revised RECIST guideline (version 1.1)," Eur. J. Cancer., 2009, 45(2):228-47.

Engel et al. "CD Nomenclature 2015: Human Leukocyte Differentiation Antigen Workshops as a Driving Force in Immunology." J. Immunology, 2015, 195:10:4555-4563.

European Search Report in European Appln. No. 20736109.8, dated Mar. 29, 2022, 15 pages.

Frankel et al. "Metagenomic shotgun sequencing and unbiased metabolomic profiling identify specific human gut microbiota and metabolites associated with immune checkpoint therapy efficacy in melanoma patients." Neoplasia, 2017, 19.10: 848-855.

Gett et al., "T cell fitness determined by signal strength," Nat. Immunol., 2003, 4:355-60.

(Continued)

*Primary Examiner* — Brian Gangle
(74) *Attorney, Agent, or Firm* — Fish & Richardson P.C.

(57) ABSTRACT

The disclosure provides therapeutic peptides and pharmaceutical compositions comprising the peptides, which have utility in treating various human diseases. In particular aspects, the disclosed therapeutic peptides are useful as immunotherapeutics for modulating regulatory and effector molecules of the mammalian immune system to mitigate disease.

10 Claims, 31 Drawing Sheets
Specification includes a Sequence Listing.

(56) References Cited

OTHER PUBLICATIONS

Gopalakrishan et al, "Gut microbiome modulates response to anti-PD-1 immunotherapy in melanoma patients," Science, 2018, 359:6371:97-103.

Humphries et al., "The gut microbiota and immune checkpoint inhibitors," Vaccin. Immunother., 2018, 14(9): 2178-2182.

Imai et al., "Transcriptional silencing and longevity protein SIR2 is an NAD-dependent histone deacetylase," Nature, 2000, 403:795-800.

International Preliminary Report on Patentability in International Appln. No. PCT/US2020/012431, dated May 28, 2020, 7 pages.

International Preliminary Report on Patentability in International Appln. No.PCT/US2020/035983, dated Dec. 21, 2021, 8 pages.

International Search Report and Written Opinion in Appln. No. PCT/US2020/012431, dated May 28, 2020, 10 pages.

International Search Report and Written Opinion in Appln. No. PCT/US2020/035983, dated Oct. 16, 2020, 9 pages.

Kaech et al., "Memory CD8+ T cell differentiation: initial antigen encounter triggers a developmental program in naïve cells," Nat. Immunol., 2001, 2:415-22.

Karpinski et al., "Anticancer activity of bacterial proteins and peptides," Pharmaceutics, 2018, 10:54.

Katlinskaya et al., "Abstract 576: A novel intestinal microbiome-derived peptide modulates host T cell activation," Cancer Res., 2019, 79.

Lanzavecchia et al., "Antigen decoding by T lymphocytes: from synapses to fate determination," Nat. Immunol., 2001, 2:487-92.

Marin-Acevedo, et al., "Next generation of immune checkpoint therapy in cancer: new developments and challenges," J. Hematol. Oncol., 2018, 11:39.

Matson et al., "The commensal microbiome is associated with anti-PD-1 efficacy in metastatic melanoma patients," Science., 2018, 359:6371:104-108.

McKeown et al., "Current Approaches and Challenges for Monitoring Treatment Response in Colon and Rectal Cancer," J. Cancer. 2014, 5(1): 31-43.

Peters et al. "Relating the gut metagenome and metatranscriptome to immunotherapy responses in melanoma patients." GenomeMedicine, 2019, 11:61: 1-14.

Pool-Zobel et al., "Overview of Experimental Data on Reduction of Colorectal Cancer Risk by Inulin-Type Fructans, "J. Nutr., 2007, 137:2580-2584.

Ramirez-Farias et al., "Effect of inulin on the human gut microbiota: stimulation of Bifidobacterium adolescentis and Faecalibacterium prausnitzii," Br. J. Nutr., 2009, 101:4:541-50.

Roychoudhuri et al. "The interplay of effector and regulatory T cells in cancer" Current Opinion in Immunology, 2015, 33:101-111.

Seymour et al., "iRECIST: guidelines for response criteria for use in trials testing immunotherapeutics," Lancet Oncol., 2017, 18(3): e143-e152.

Sivan et al., "Commensal Bifidobacterium promotes antitumor immunity and facilitates anti-PD-L1 efficacy," Science, 2015, 350(6264):1084-1089.

Steinman et al., "Tolerogenic dendritic cells," Annu. Rev. Immunol., 2003, 21:685-711.

Thallinger et al., "Review of cancer treatment with immune checkpoint inhibitors: Current concepts, expectations, limitations and pitfalls," Wien Klin Wochenschr. 2018; 130(3): 85-91.

Uniprot Accession No. A0A087DKK6, "Anhydro-N-acetylmuramyl-tripeptide amidase," XP055902159, Jun. 7, 2017, 1 page.

Uniprot Accession No. D4BRT0, "Uncharacterized protein," XP055902164, Feb. 2, 2018, 1 page.

Uniprot Accession No. A0A0AOUUZ4, "Uncharacterized protein" from Bifildobacterium bereve 1 page.

Valenzuela et al., "The Roles of IL-12 in Providing a Third Signal for Clonal Expansion of Naive CD8 T Cells," 2002, J. Immunol., 169:6842-9.

Van Stipdonk et al., "Naïve CTLs require a single brief period of antigenic stimulation for clonal expansion and differentiation," Nat. Immunol., 2001, 2:423-9.

Wolchok et al., "Guidelines for the Evaluation of Immune Therapy Activity in Solid Tumors: Immune-Related Response Criteria," Clin. Cancer Res., 2009, 1;15(23):7412-20.

Zhang et al., "Cytokines, Inflammation and Pain," Int. Anesthesiol. Clin., vol. 45(2):27-37, Spring 2007.

PCT International Search Report and Written Opinion in International Appln. No. PCT/US2022/032236, mailed on Oct. 11, 2022, 12 pages.

Allali et al., "Gut microbiome of Moroccan colorectal cancer patients," Medical Microbiology and Immunology, Aug. 2018, 207:211-25.

Awan et al., "Identification of circulating biomarker candidates for hepatocellular carcinoma (HCC): an integrated prioritization approach," PloS One, Sep. 2015, 10(9):e0138913, 26 pages.

Dhankhar et al., "In-silico approach to identify novel potent inhibitors against GraR of S. aureus," Frontiers in Bioscience-Landmark, Mar. 2020, 25(7):1337-60.

El-Halfawy et al., "Discovery of an antivirulence compound that reverses β-lactam resistance in MRSA," Nature Chemical Biology, Feb. 2020, 16(2):143-9.

EP European Search Report in European Appln. No. 21821256.1, mailed on Jun. 24, 2024, 21 pages.

Makarova et al., "Two C or not two C: recurrent disruption of Zn-ribbons, gene duplication, lineage-specific gene loss, and horizontal gene transfer in evolution of bacterial ribosomal proteins," Genome Biology, Aug. 30, 2001, 2(9), 14 pages.

Panina et al., "Comparative genomics of bacterial zinc regulons: enhanced ion transport, pathogenesis, and rearrangement of ribosomal proteins," Proceedings of the National Academy of Sciences, Aug. 2003, 100(17):9912-7.

CN Office Action in Chinese Appln. No. 202080008055.0, mailed on Jul. 24, 2024, 13 pages (with English translation).

NCBI Accession No. WP_003830471.1, "hypothetical protein [Bifidobacterium breve]," May 26, 2016, 1 page.

T Cell Activation, In Vitro

Experimental Procedure

Step I: Antibody Coating of the Assay Plate Microwells:
1. Prepare a solution of anti-mouse or -human CD3e in sterile PBS. Calculate the number of wells required for each experimental condition and consider triplicate samples for each condition.
2. Dispense 2 mL of the antibody solution to each well of the 12-well assay plate. For the control unstimulated wells, use sterile PBS or Isotype Control Antibodies.
3. Tightly cover the plate with Parafilm™ to avoid sample evaporation and incubate at 4°C overnight.
4. Before adding cells, remove the antibody solution.
5. Rinse each well with 3 mL of sterile PBS 3X and discard PBS.

Step II: Addition of Cells:
1. Prepare your cells of interest under sterile conditions.
2. Count cells and resuspend in AIM media.
3. After washing the wells with PBS (step 5 above), add 2 mL of the cell suspension to each well and place in a humidified 37°C, 5% CO2 incubator.
4. Incubate for 2 days.
5. Supernatants can be collected and store -80°C.
6. Cells can be harvested and processed

FIG. 5A

Flow Cytometry:

1. Isolate mouse or human cells according to the their specific protocols.

2. Wash the cells in cold PBS and pellet the cells by centrifugation (e.g., 400 x g at 4°C, 5 min). Resuspend the cell pellet with cold PBS to a final concentration of 2 x 10e7 cells/ml.

3. Distribute 100 μl aliquots of the cell suspension (around 0.3-10e6 cells/well) to deep well plates.

4. Stain the cells in 100 μl of Live/Dead Stain for 15-20 min on ice protected from light.

5. Wash the cells with 500 μl of cold Stain Buffer.

6. Reconstitute the pellets in 100 μl of Stain Buffer and incubate with 10 μl FcR blocking reagent for 15-20 min on ice.

7. Prior to adding antibody cocktail, add 50 μl of Brilliant Stain Buffer to each well. Prepare antibody cocktails as recommended by manufacture in Stain Buffer and add 100 μl aliquots of the diluted antibodies to the wells that contain the target cell suspensions. Incubate for 40 minutes on ice protected from light.

8. Wash the cells with 500 μl of Stain Buffer to remove unbound antibodies. Centrifuge cells as 400 x g for 5 min. After each centrifugation, carefully invert supernatants from cell pellets.

9. Fix the cells in 300 μl of BD Cytofix™ Fixation Buffer for 40 minutes on ice protected from light.

10. Wash the cells once with 500 μl of Stain Buffer.

11. Reconstitute in 300μl of Stain Buffer in U-bottom microwell plate for flow cytometry analysis.

FIG. 5B

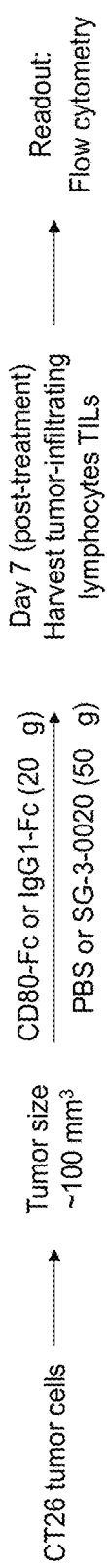
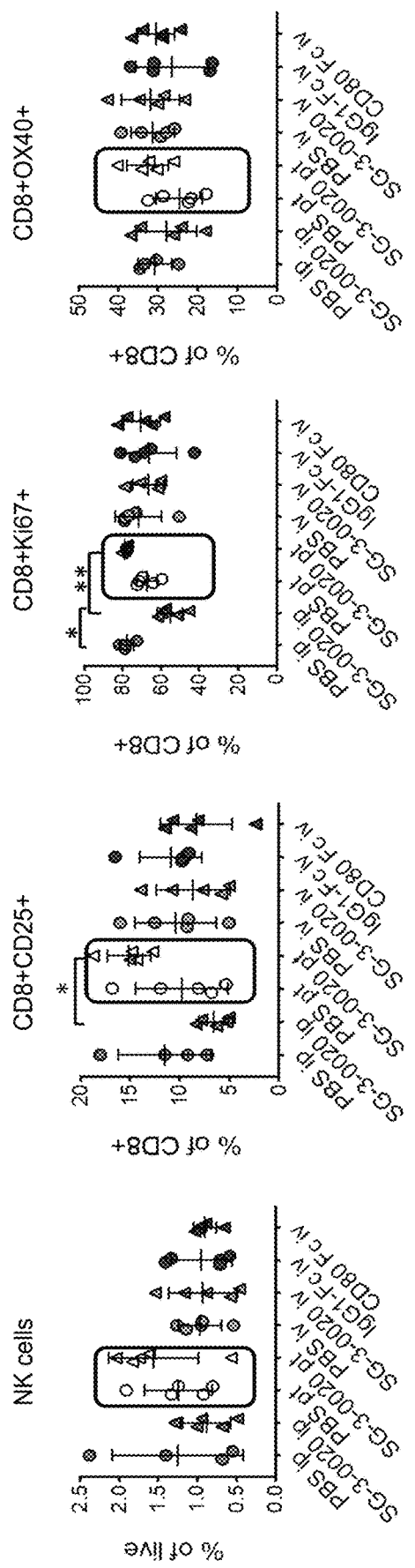
FIG. 7A
FIG. 7B

AH-1 tetramer staining:

1. Isolate cells according to the their specific protocols.
2. Wash the cells in cold PBS and pellet the cells by centrifugation (e.g., 400 x g at 4°C, 5 min). Resuspend the cell pellet with cold PBS to a final concentration of 2 x 10e7 cells/ml.
3. Distribute 100 µl aliquots of the cell suspension (around 0.3-10e6 cells/well) to deep well plates.
4. Stain the cells in 100 µl of Live/Dead Stain for 15-20 min on ice protected from light.
5. Wash the cells with 500 µl of cold Stain Buffer.
6. Reconstitute the pellets in 100 µl of Stain Buffer and incubate with 10 µl FcR blocking reagent for 15-20 min on ice.
7. Pre-dilute H-2Ld MuLV gp70 Tetramer-PE (MBL, PN TS-M521-1) or control tetramer 1:20 in FACS buffer and add 5 ul to the staining wells and 5 ul of stain buffer to the control wells. Incubate for 30 minutes on ice.
8. Add 1 µL of anti-CD8 FITC (clone KT15) to each well. Pulse vortex gently to mix
9. Incubate for at least 20 minutes on ice.
10. Wash the cells with 500 µl of Stain Buffer to remove unbound antibodies. Centrifuge cells as 400 x g for 5 min. After each centrifugation, carefully invert supernatants from cell pellets.
11. Wash the cells once with 500 µl of Stain Buffer.
12. Reconstitute in 300µl of Stain Buffer in U-bottom microwell plate for flow cytometry analysis.

FIG. 8

Flow Cytometry. T cell panel. CD8+ proportion
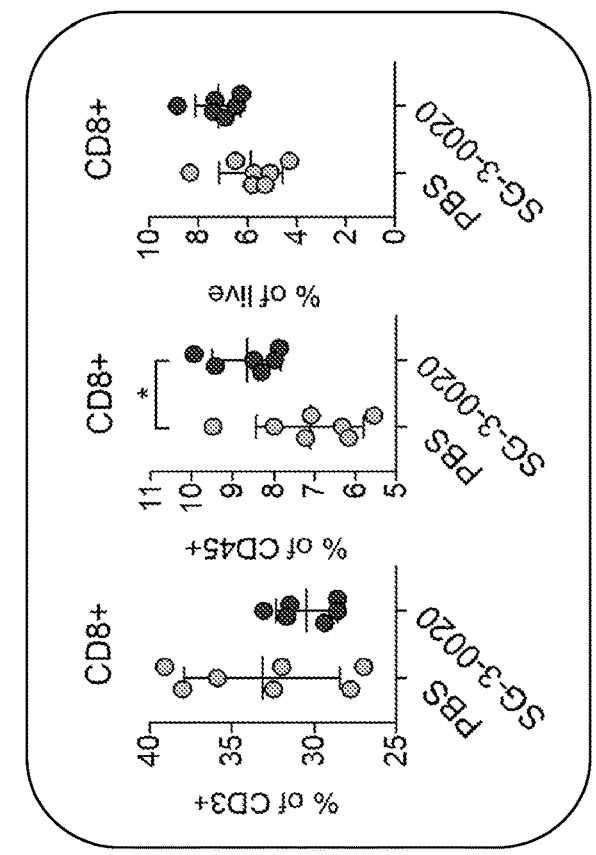
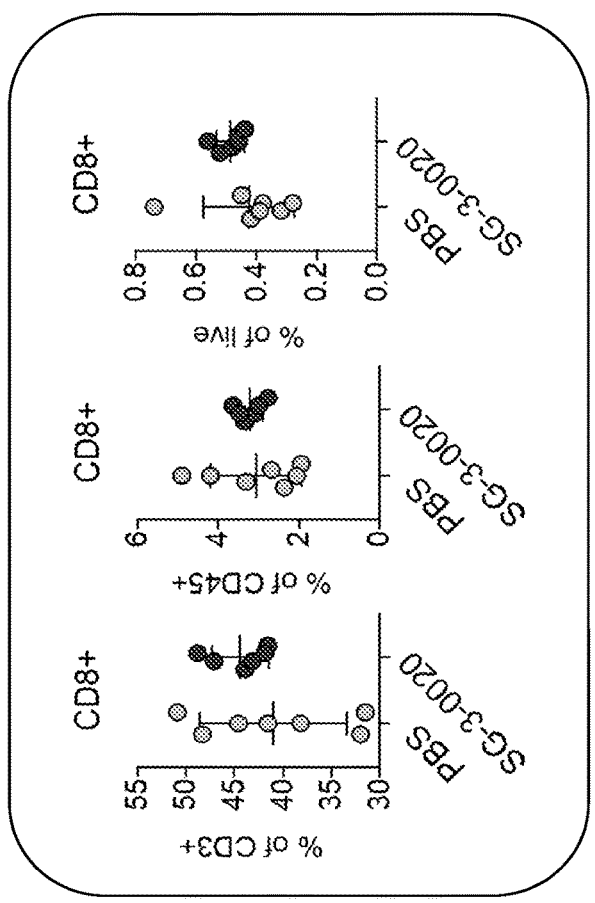
FIG. 10

```
                        SEQUENCE LISTING

<160> NUMBER OF SEQ ID NOS: 2

<210> SEQ ID NO 1
<211> LENGTH: 42
<212> TYPE: PRT
<213> ORGANISM: Bifidobacterium breve

<400> SEQUENCE: 1

Met Leu Ser Thr Lys Lys Thr Lys Thr His Asp His Tyr Pro Cys Gly
1               5                   10                  15

Arg Met Arg Asp Pro Gly Trp His Asp Trp Arg Ala Cys Leu Thr His
            20                  25                  30

Gln Gly Ile Glu Glu Asp Glu Trp Pro Val
        35                  40

<210> SEQ ID NO 2
<211> LENGTH: 126
<212> TYPE: DNA
<213> ORGANISM: Bifidobacterium breve

<400> SEQUENCE: 2
atgttgagta ccaagaagac caagacccac gaccactacc cgtgcggccg catgcgcgac      60
cccggctggc acgactggcg cgcctgtctc acccaccaag gcatcgagga ggatgaatgg     120
ccggtc                                                                126
```

MICROBIALLY DERIVED PEPTIDES AND PROTEINS FOR IMMUNOTHERAPY

CROSS-REFERENCE TO RELATED APPLICATIONS

This application is a National Stage Application under 35 U.S.C. § 371 and claims the benefit of International Application No. PCT/US2020/012431, filed Jan. 6, 2020, which claims priority to U.S. Provisional Application No. 62/788,950 filed on Jan. 6, 2019. The entire contents of the foregoing applications are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: 47192 0015US1 Sequence-Listing.txt, date created, Apr. 2, 2021, file size ~ 4 kilobytes.

FIELD

The present disclosure relates to novel peptides and pharmaceutical compositions comprising said peptides that have application, inter alia, in the treatment of diseases associated with the mammalian adaptive and innate immune system and immunology-associated disorders. In some embodiments, the peptides and pharmaceutical compositions described herein have particular application in the treatment or prevention of immuno-oncology disease states such as primary and metastatic neoplastic diseases.

BACKGROUND

Inflammatory and immune-related diseases are the manifestation or consequence of complex and often multiple interconnected biological pathways, which in normal physiology are critical to respond to injury or insult, initiate repair from injury or insult, and mount an innate and/or acquired defense against foreign organisms. Disease or pathology occurs when these normal physiological pathways cause additional injury or insult directly related to the intensity of the response, as a consequence of abnormal regulation or excessive stimulation, as a reaction to self, or as a combination thereof.

While the genesis of these diseases often involves multistep pathways and often multiple biological systems or pathways, intervention at critical points in one or more of these pathways can have an ameliorative or therapeutic effect. Therapeutic intervention can occur by either antagonism of a detrimental process/pathway or stimulation of a beneficial process/pathway. Many immune-related diseases are known and have been extensively studied. Such diseases include inflammatory diseases, infectious diseases, immunodeficiency diseases, neoplastic diseases, etc.

Cancer is the second leading cause of death, resulting in one out of every four deaths in the United States. More than one million people in the U.S. get cancer each year, and in 2016, it was estimated that 595,690 cancer deaths occurred. Due to the ever-increasing aging population in the U.S., it is reasonable to expect that rates of cancer incidence will continue to grow. See American Cancer Society.

Cancer is a disease which involves the uncontrolled growth (i.e., division) of cells. Some of the known mechanisms which contribute to the uncontrolled proliferation of cancer cells include growth factor independence, failure to detect genomic mutation, and inappropriate cell signaling. The ability of cancer cells to ignore normal growth controls may result in an increased rate of proliferation. Although the causes of cancer have not been firmly established, there are some factors known to contribute, or at least predispose a subject, to cancer. Such factors include particular genetic mutations (e.g., BRCA gene mutation for breast cancer, APC for colon cancer), exposure to suspected cancer-causing agents, or carcinogens (e.g., asbestos, UV radiation) and familial disposition for particular cancers such as breast cancer.

Cancer is currently treated using a variety of modalities including surgery, radiation therapy and chemotherapy. The choice of treatment will depend upon the type, location and dissemination of the cancer. For example, surgery and radiation therapy may be used to treat non-solid tumor cancers such as leukemia and lymphoma. One of the advantages of surgery and radiation therapy is the ability to control to some extent the impact of the therapy, and thus to limit the toxicity to normal tissues in the body. However, surgery and radiation therapy are often followed by chemotherapy to guard against any remaining or radio-resistant cancer cells. Chemotherapy is also the most appropriate treatment for disseminated cancers such as leukemia and lymphoma, as well as metastases.

Because many chemotherapy agents target cancer cells based on their proliferative profiles, tissues such as the gastrointestinal tract and the bone marrow which are normally proliferative are also susceptible to the effects of the chemotherapy.

Many chemotherapeutic agents have been developed for the treatment of cancer. Not all tumors, however, respond to chemotherapeutic agents and others, although initially responsive to chemotherapeutic agents, may develop resistance. As a result, the search for effective anti-cancer drugs has intensified in an effort to find even more effective agents with less non-specific toxicity.

Thus, there is a great need to develop additional and safer cancer therapeutics that leverage aspects of the mammalian immune system to aid in treating and preventing cancer. Despite new cancer treatments coming to market each year, these treatments are further accompanied by problematic side effects.

SUMMARY OF THE DISCLOSURE

The present disclosure addresses this important need in the medical community, by providing novel peptide therapeutics that are able to modulate the immune response of a subject, and utilize said immune response in a beneficial way to treat a disease in the subject.

This disclosure provides a microbial peptide and variants thereof that modulate immunoregulatory cells, including but not limited to T cells, effector T cells and dendritic cells, to aid in cancer treatments and other immune-associated disorders and diseases.

Thus, to address the problems outlined above, the disclosure provides an immunotherapeutic pharmaceutical composition for modulating regulatory and effector cells and molecules of the mammalian immune system to treat disease. In some embodiments, that disease is cancer.

The peptide therapeutics provided herein are useful in treating the numerous diseases that are associated with inflammatory immune responses and immune-oncology.

In some embodiments, the present disclosure is drawn to an immunotherapeutic composition for modulating regulatory and effector molecules of the mammalian immune system to treat a disease, comprising: a purified therapeutic protein comprising an amino acid sequence referred to herein as SEQ ID NO:1 or SG-3-0020. The present disclosure encompasses a protein comprising an amino acid sequence having at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:1. In some embodiments, the therapeutic protein is less than 100% identical to SEQ ID NO:1. In other embodiments, the therapeutic protein comprises 1, 2, 3, 4, or 5 amino acid substitutions relative to the amino acid sequence identified in SEQ ID NO:1. In yet other embodiments, the therapeutic protein which is less than 100% identical to SEQ ID NO:1 retains one or more activities of the full length peptide consisting of the amino acid sequence of SEQ ID NO:1.

In some embodiments, the immunotherapeutic composition (or therapeutic protein) activates immune cells in an in vitro assay comprising incubation of the therapeutic protein with the immune cells. In other embodiments, the immune cells are human or rodent immune cells. In still other embodiments, the rodent immune cells are mouse immune cells. In some embodiments, the immune cells are peripheral blood mononuclear cells (PBMCs). In other embodiments, the immune cells are lymphocytes and/or monocytes. In yet other embodiments, the immune cells are dendritic cells.

In some embodiments, incubation of the therapeutic protein (or composition comprising the therapeutic protein) with an immune cell in vitro results in a change in the production or secretion of TNF-α, IL-17, IL-1β, IL-2, IFN-γ, IL-6, IL-12, IL-25, IL-33, IL-8, MCP-1, MIP-3α, CXCL1, IL-23, IL-4, IL-10, IL-13, IFN-α, and/or TGF-β by the immune cell.

In some embodiments, the immune cells are selected from the group consisting of T cells and NK cells. In some embodiments, the T cells are CD3-activated T cells (T cells activated by contact with an anti-CD3 immunoglobulin). In some embodiments, the activation of T cells comprises an increase in secretion one or more cytokines. In other embodiments, the one or more cytokines is selected from the group consisting of IFN-γ and IL-2.

In some embodiments, the immunotherapeutic composition (or therapeutic protein) increases cytokine secretion by a CD3-activated T cell in an in vitro assay. In other embodiments, the increased cytokine secretion is relative to cytokine secretion by the CD3-activated T cell in the absence of the therapeutic peptide. In still other embodiments, the increased cytokine secretion is an increase of at least 5%, 10%, 20%, 25%, 30%, 40% or 50% over the cytokine secretion by the CD3-activated T cell in the absence of the therapeutic peptide. In some embodiments, the increased cytokine secretion comprises an increase in the secretion of a cytokine selected from the group consisting of IFN-γ, IL-2, IL-10, and TNF-α.

In some embodiments, the composition activates immune cells in a subject administered the composition. In other embodiments, the activation of immune cells comprises an increase in the number of immune cells in a tumor microenvironment. In still other embodiments, the increase of the number of immune cells in the tumor microenvironment comprises an increase of immune cell frequency of tumor infiltrated lymphocytes (TILs). In yet other embodiments, the TILs comprise NK cells and/or activated CD8+ T cells.

In some embodiments, the composition further comprises a pharmaceutically acceptable carrier.

In one aspect, a polynucleotide is provided, wherein the polynucleotide comprises a nucleotide sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2. In some embodiments, the nucleotide sequence is less than 90%, 91%, 92%, 93%, 94%, 95%, 96%, 97%, 98%, 99%, or 100% identical to SEQ ID NO:2. For example, in some embodiments, the polynucleotide comprises a nucleotide sequence that is at least 50%, 60%, 65%, 70%, 75%, 80%, 85% or 90% identical to SEQ ID NO:2 and less than 90%, 91%, 92%, 93%, 94%, 95%, 96%, 97%, 98%, 99%, or 100% identical to SEQ ID NO:2.

In some embodiments, the polynucleotide comprises a nucleotide sequence that encodes a protein which has at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:1. In some embodiments, the polynucleotide sequence encodes a protein that is less than 100% identical to SEQ ID NO:1. For example, the polynucleotide comprises a nucleotide sequence that encodes a protein that has less than 100% identical to SEQ ID NO:1 and at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:1. In yet other embodiments, the polynucleotide sequence which encodes the protein is codon-optimized such that the codons of SEQ ID NO:2 are modified for optimal expression of SEQ ID NO:1 in an expression system, but wherein the codon-optimized nucleotide sequence is not 100% identical to SEQ ID NO:2. In still other embodiments, the expression system is a prokaryotic or a eukaryotic expression system. In some embodiments, the prokaryotic system comprises *Escherichia coli*.

In some embodiments, the therapeutic peptide of the disclosure is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence depicted in SEQ ID NO:1. In some embodiments, a therapeutic peptide of the disclosure shares 100% sequence identity with SEQ ID NO:1.

In some embodiments, the therapeutic peptide of the disclosure comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:1, and retains one or more activities of the full length peptide consisting of the amino acid sequence depicted in SEQ ID NO:1.

In some embodiments, the therapeutic peptide of the disclosure comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:1, and has the functional ability to increase secretion of IL-2 and/or IFN-γ when administered to a subject in need thereof.

In some embodiments, the therapeutic peptide of the immunotherapeutic pharmaceutical composition induces the production of at least one pro-inflammatory cytokine, in a subject administered the peptide. In some embodiments, the peptide of the immunotherapeutic pharmaceutical composition induces the production of at least one pro-inflammatory cytokine in a subject administered the peptide, wherein the at least one cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the therapeutic peptide of the immunotherapeutic pharmaceutical composition suppresses the production of at least one anti-inflammatory cytokine, in a subject administered the peptide. In some embodiments, the peptide of the immunotherapeutic pharmaceutical composition suppresses the production of at least one anti-inflammatory cytokine in a subject administered the peptide, wherein the at least one cytokine is selected from the group consisting of IL-4, IL-10, IL-13, IFN-α, and TGF-β.

In some embodiments, the therapeutic peptide of the present disclosure, when administered to a subject in need thereof, increases one or more T cells selected from the group consisting of CD4+CD25+, CD4+PD-1+, CD4+ ICOS+, CD4+OX40+, CD8+CD25+, CD8+PD-1+, CD8+ ICOS+, and CD8+OX40+. In other embodiments, the therapeutic peptide of the present disclosure, when administered to a subject in need thereof, increases secretion of one or more cytokines selected from the group consisting of IFN-γ, IL-2, IL-10 and TNF-α.

In some embodiments, the composition is a pharmaceutical composition formulated for intravenous, subcutaneous, local, or oral administration. In other embodiments, the composition is a pharmaceutical composition formulated for administration to a tumor microenvironment.

In some embodiments, the composition is formulated as a liquid, solid, semi-solid, gel, or lotion.

In one aspect, a method of modulating an in vivo immune response in a subject is provided, wherein the method comprises administering to the subject a composition comprising the SG-3-0020 protein or variant thereof as described.

In some embodiments, the modulating of the in vivo immune response comprises a change in the blood or plasma level of one or more cytokines selected from the group consisting of: TNF-α, IL-17, IL-1β, IL-2, IFN-γ, IL-6, IL-12, IL-25, IL-33, IL-8, MCP-1, MIP-3α, CXCL1, IL-23, IL-4, IL-10, IL-13, IFN-α, and TGF-β.

In one aspect, a method of treatment is provided comprising administering to a subject in need thereof a composition comprising a protein comprising an amino acid sequence having at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1. In some embodiments, the subject in need thereof has been diagnosed with or is at risk of developing a disease or disorder selected from the group consisting of: colorectal cancer (CRC), non small cell lung carcinoma (NSCLC), melanoma, basal cell carcinoma, biliary tract cancer, bladder cancer, bone cancer, brain and central nervous system cancer, breast cancer, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, small-cell lung cancer, Hodgkin's lymphoma, non-Hodgkins lymphoma, myeloma, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, cancer of the urinary system, and any combination of two or more thereof.

In some embodiments, the SG-3-0020 protein or variant thereof is administered to the subject prior to and/or in conjunction with an immunotherapy. In other embodiments, the immunotherapy is one or more of an anticancer vaccine, an adoptive immune cell therapy, an agent that targets an immune checkpoint regulator, an oncolytic virus or a BiTE. In still other embodiments, the immunotherapy targets are one or more of CTLA-4 (cytotoxic T-lymphocyte-associated protein 4), PD-1 (Programmed cell death protein 1), PD-L1 (Programmed death-ligand 1), BTLA (B and T lymphocyte attenuator), LAG-3 (Lymphocyte Activation Gene 3), A2AR (Adenosine A2a receptor), TIM-3 (T-cell immunoglobulin and mucin domain-3), B7-H3 (B7 homolog 3; also known as CD276), VISTA (V-domain Ig suppressor of T cell activation), and IDO (indoleamine 2,3-dioxygenase), or an immune checkpoint regulator. In some embodiments, the immunotherapy is a dual PD-1/CTLA-4 blockade therapy. In some embodiments, the immunotherapy is a PDL-1 treatment for subjects with PDL1+ tumors or dual PD-1/PD-L1 blockade. Nonlimiting examples include but are not limited to PD-1 and PDL-1 antagonists such as antibodies (e.g., pembrolizumab (KEYTRUDA®), nivolumab (OPDIVO®), cemiplimab (LIBTAYO®), atezolizumab (TECENTRIQ®), avelumab (BAVENCIO®), and durvalumab (IMFINZI®)). In some embodiments the checkpoint inhibitor is a CTLA4 antagonist such as an antibody (e.g., ipilumumab (YERVOY®)). In some embodiments the checkpoint inhibitor is a BTLA antagonist such as an antibody. In some embodiments the checkpoint inhibitor is a LAG-3 antagonist (e.g., IMP701 (LAG525)). In some embodiments the checkpoint inhibitor is an A2AR antagonist (e.g., CPI-444). In some embodiments the checkpoint inhibitor is a TIM-3 antagonist (e.g., MBG453). In some embodiments the checkpoint inhibitor is a B7-H3 antagonist such as an antibody (e.g., enoblituzumab). In some embodiments the checkpoint inhibitor is a VISTA antagonist (e.g., JNJ-61610588). In some embodiments the checkpoint inhibitor is an IDO antagonist (e.g., indoximod). See, for example, Marin-Acevedo, et al., J Hematol Oncol. 11: 39 (2018). In some embodiments, the immunotherapy is an adoptive T cell therapy including but not limited to chimeric antigen receptor T cells (e.g., CAR-T cells) or engineered TCR-T cells. In some embodiments, the immunotherapy is a Bispecific T cell Engagers (BiTE). In some embodiments, the immunotherapy includes one or more of anti-lymphocyte activation gene3 (LAG-3) therapy, anti-T cell immunoglobin mucin-3 (TIM-3) therapy, anti-killer immunoglobin-like receptors (KIR) therapy, anti-4-1BB (CD137) agonizing/stimulatory therapy, or glucocorticoid-induced TNFR family related gene (GITR) agonizing/stimulatory therapy—each alone or in combinations with each other, and/or in combination with one or more of PD-1, PDL-1, CTLA-4 or other therapies.

In some embodiments, the therapeutic protein of the immunotherapeutic pharmaceutical composition modulates the production of at least one cytokine, in a subject administered the peptide. In other embodiments, the peptide of the immunotherapeutic pharmaceutical composition modulates the production of at least one cytokine in a subject administered the peptide, wherein the at least one cytokine is selected from the group consisting of TNF-α, IL-17, IL-1β, IL-2, IFN-γ, IL-6, IL-12, IL-25, IL-33, IL-8, MCP-1, MIP-3α, CXCL1, IL-23, IL-4, IL-10, IL-13, IFN-α, and TGF-β. In still other embodiments, the modulation of production of the at least one cytokine is measured by measuring the blood and/or plasma levels of the one or more cytokines in the subject blood.

In some embodiments, the therapeutic protein of the immunotherapeutic pharmaceutical composition increases Th1 activation in a subject administered the peptide. In some embodiments, the peptide of the immunotherapeutic pharmaceutical composition increases dendritic cell maturation, in a subject administered the peptide. In some embodiments, the peptide of the immunotherapeutic pharmaceutical composition increases CD70 expression, in a subject administered the peptide. In some embodiments, the peptide of the immunotherapeutic pharmaceutical composition increases the clonal expansion of $T_{eff}$, in a subject administered the peptide.

In some embodiments, the pharmaceutical composition is formulated for oral administration. In other embodiments, the pharmaceutical composition is formulated for parenteral administration. In still other embodiments, the parenteral administration is intravenous, subcutaneous, or transdermal administration.

BRIEF DESCRIPTION OF THE FIGURES

FIG. 5A shows a protocol for in vitro activation of the human T cells and FIG. 5B shows a protocol used for flow cytometry analysis.

FIGS. 7A and 7B illustrate in vivo studies and exemplary results of administration of a therapeutic peptide such as SG-3-0020 on activation of human to a mouse tumor model.

FIG. 8. shows an exemplary protocol for AH-1 tetramer staining.

FIGS. 9-10 illustrate in vivo studies and exemplary results of administration of a therapeutic peptide such as SG-3-0020 on activation of human to a mouse tumor model.

FIG. 16A is a volcano plot shows upregulated (right) and downregulated (left) differentially expressed genes (DEGs) in SG-3-0020 treated group (10 µM) compared to vehicle-treated group. Genes that are significant (p<0.05) with >2-fold change (log 2FC=1) are labeled. FIG. 16B shows selected examples of immune-oncology relevant DEGs.

DETAILED DESCRIPTION

Definitions

Figure 1:
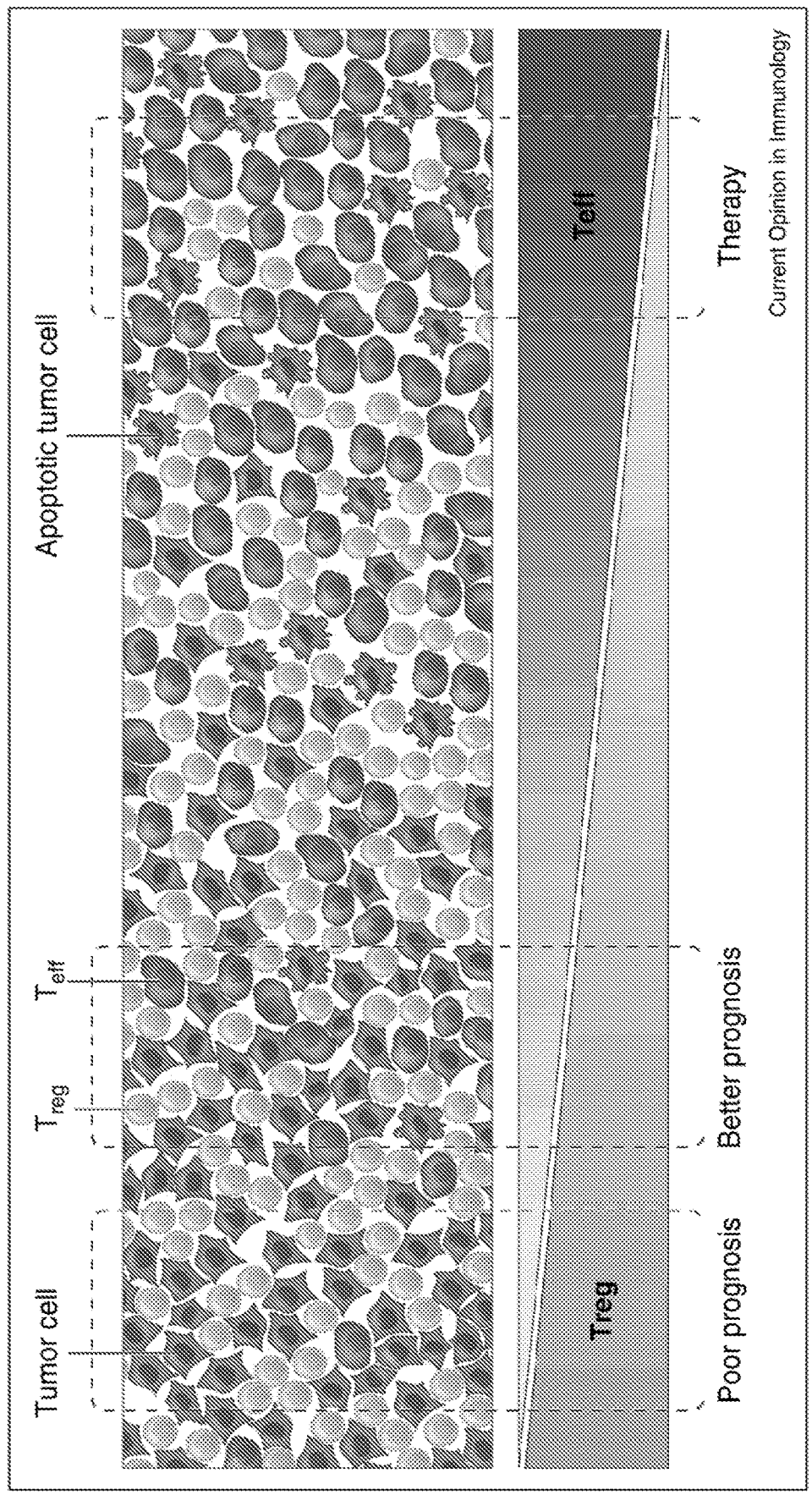
FIG. 1 provides an illustration of the balance of regulatory and effector T cells.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art. Thus, while the following terms are believed to be well understood by one of ordinary skill in the art, the following definitions are set forth to facilitate explanation of the presently disclosed subject matter.

Throughout this specification, the word "comprise" or variations such as "comprises" or "comprising" will be understood to imply the inclusion of a stated component, or group of components, but not the exclusion of any other components, or group of components.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The term "including" is used to mean "including but not limited to." "Including" and "including but not limited to" are used interchangeably.

The terms "peptide," "polypeptide," and "protein" are used interchangeably herein and each refers broadly to a sequence of amino acids joined together by peptide bond as is well understood by the ordinarily skilled artisan. It should be understood that this term does not connote a specific length of a polymer of amino acids.

A "signal sequence" (also termed "presequence," "signal peptide," "leader sequence," or "leader peptide") refers to a sequence of amino acids bound to the N-terminal portion of a protein, which facilitates the secretion of the mature form of the protein from the cell. The mature form of the extracellular protein lacks the signal sequence, which is cleaved off during the secretion process.

The term "amino acid" or "any amino acid" refers to any and all amino acids, including naturally occurring amino acids (e.g., a-amino acids), unnatural amino acids, modified amino acids, and non-natural amino acids. It includes both D- and L-amino acids.

The recitations "sequence identity," "percent identity," "percent homology," or for example, comprising a "sequence 50% identical to," as used herein, refer to the extent that sequences are identical on an amino acid-by-amino acid basis, or a nucleotide-by-nucleotide basis, or over a window of comparison. Thus, a "percentage of sequence identity" may be calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes. The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6.0), using a PAM120 weight residue table, a gap length penalty of 12 and a gap penalty of 4.

The phrases "substantially similar" and "substantially identical" in the context of at least two nucleic acids or polypeptides typically means that a polynucleotide or polypeptide comprises a sequence that has at least about 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference polynucleotide or polypeptide.

Related (and derivative) proteins/peptides encompass "variant" proteins/peptides. Variant proteins/peptides differ from another (i.e., parental) protein/peptide and/or from one another by a small number of amino acid residues. A variant may include one or more amino acid mutations (e.g., amino acid deletion, insertion or substitution) as compared to the parental protein/peptide from which it is derived. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein/peptide or nucleic acid, e.g., as determined using a sequence alignment tool, such as the previously discussed BLAST, ALIGN, and CLUSTAL. For example, variant proteins/peptides or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence. In some embodiments, variant proteins/peptides or nucleic acids are not 100% identical to a reference sequence.

The term "pharmaceutically acceptable salt," as used herein, represents salts or zwitterionic forms of the peptides, proteins, or compounds of the present disclosure, which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

As used herein, the term "chimeric" or "recombinant" when describing a nucleic acid sequence, or a protein/peptide sequence, refers to a nucleic acid, or a protein/peptide sequence, which links at least two heterologous polynucleotides, or two heterologous polypeptides, into a single macromolecule, or that re-arranges one or more elements of at least one natural nucleic acid or protein/peptide sequence. For example, the term "recombinant" can refer to an artificial combination of two otherwise separated segments of sequence, e.g., by chemical synthesis or by the manipulation of isolated segments of nucleic acids by genetic engineering techniques.

As used herein, the term "protein modification" refers to, e.g., amino acid substitution, amino acid modification, deletion, and/or insertion, as is well understood in the art.

The term "culturing" refers to growing a population of cells, e.g., microbial cells, under suitable conditions for growth, in a liquid or solid medium.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system.

The term "subject" refers to a mammal such as a human, a non-human primate, a livestock animal (e.g., bovine, porcine), a companion animal (e.g., canine, feline) and a rodent (e.g., a mouse and a rat). In some embodiments, the term refers to a human subject. In exemplary embodiments, the term refers to a human subject that suffers from a gastrointestinal inflammatory condition.

As used herein, the term "host cell" refers to a cell or cell line into which a recombinant expression vector for production of a peptide may be introduced for expression of the peptide. A host cell comprising a recombinant vector can be referred to as a "recombinant host cell."

As used herein, "improved" should be taken broadly to encompass improvement in an identified characteristic of a disease state, said characteristic being regarded by one of skill in the art to generally correlate, or be indicative of, the disease in question, as compared to a control, or as compared to a known average quantity associated with the characteristic in question. For example, "improved" function associated with application of a protein of the disclosure can be demonstrated by comparing the data from a human treated with a protein of the disclosure, as compared to the data of a human not treated. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments. Thus, an "inhibited immune response" or the "inhibition of inflammatory cytokines" does not require absolute inhibition.

Thus, as used herein, the terms "increase" or "reduce," or grammatical equivalents, indicate values that are relative to a reference (e.g., baseline) measurement, such as a measurement taken under comparable conditions (e.g., in the same subject prior to initiation of treatment described herein, or a measurement in a control subject (or multiple control subjects) in the absence of treatment) described herein. In some embodiments, a suitable control is a baseline measurement, such as a measurement in the same subject prior to initiation of the treatment described herein, or a measurement in a control subject (or multiple control subjects) in the absence of the treatment described herein.

As used herein, the term "therapeutically effective amount" refers to an amount of a therapeutic agent (e.g., a peptide, polypeptide, or protein of the disclosure), which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of, or feels an effect). In some embodiments, "therapeutically effective amount" refers to an amount of a therapeutic agent or composition effective to treat or ameliorate a relevant disease or condition, and/or to exhibit a detectable therapeutic or preventative effect, such as by ameliorating symptoms associated with the disease and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular subject may depend upon a variety of factors including the particular form of disease being treated; the severity of the condition or precondition; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts. The current disclosure utilizes therapeutically effective amounts of novel peptides, and compositions comprising same, to treat a variety of diseases, such as a variety of cancers. The therapeutically effective amounts of the administered peptide, or compositions comprising same, will in some embodiments reduce incidence of said cancer.

As used herein, the term "treatment" (also "treat" or "treating") refers to any administration of a therapeutic agent (e.g., a peptide, polypeptide, or protein of the disclosure), according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., chronic or recurring immune response and inflammation of the gastrointestinal (GI) tract); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

"Pharmaceutical" implies that a composition, reagent, method, and the like, are capable of a pharmaceutical effect, and also that the composition is capable of being administered to a subject safely. "Pharmaceutical effect," without limitation, can imply that the composition, reagent, or method, is capable of stimulating a desired biochemical, genetic, cellular, physiological, or clinical effect, in at least one subject, such as a mammalian subject, for example, a human, in at least 5% of a population of subjects, in at least 10%, in at least 20%, in at least 30%, in at least 50% of subjects, and the like.

"Pharmaceutically acceptable" means approved by a regulatory agency of the Federal or a state government or listed in the U.S. Pharmacopoeia or other generally recognized pharmacopoeia for safe use in animals, and more particularly safe use in humans. "Pharmaceutically acceptable vehicle" or "pharmaceutically acceptable excipient" refers to a diluent, adjuvant, excipient or carrier with which a peptide as described herein is administered.

"Prophylaxis" means a measure taken for the prevention of a disease or condition or at least one symptom thereof.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease, or causing the symptom to develop with less severity than in absence of the treatment). "Prevention" or "prophylaxis" may refer to delaying the onset of the disease or disorder.

"Prophylactically effective amount" means the amount of a compound, i.e., a peptide as described herein, that when administered to a subject for prevention of a disease or condition, is sufficient to effect such prevention of the disease or condition or to prevent development of at least one symptom of the disease or condition or effect development of the symptom at a lower level of severity than in the absence of administration of the compound. The "prophylactically effective amount" can vary depending on the compound, the disease and its severity, and the age, weight, etc., of the subject to be treated.

The therapeutic pharmaceutical compositions provided herein may be derived from or comprise one or more natural products. However, in some embodiments, the therapeutic pharmaceutical compositions themselves do not occur in nature. Further, in some embodiments, the therapeutic pharmaceutical compositions possess markedly different characteristics, as compared to any individual naturally occurring counterpart, or composition component, which may exist in nature. That is, in some embodiments, the pharmaceutical compositions provided herein—which comprise a therapeutically effective amount of a purified protein or peptide—possess at least one structural and/or functional property that impart markedly different characteristics to the composition as a whole, as compared to any single individual component of the composition as it may exist naturally. The courts have determined that compositions comprising natural products, which possess markedly different characteristics as compared to any individual component as it may exist naturally, are statutory subject matter. Thus, the disclosed therapeutic pharmaceutical compositions as a whole possess markedly different characteristics. These characteristics are illustrated in the data and examples provided herein The term "T cell-mediated disease" means a disease in which T cells directly or indirectly mediate or otherwise contribute to a morbidity in a mammal. The T cell-mediated disease may be associated with, but not limited to, cell-mediated effects, lymphokine-mediated effects, and even effects associated with B cells if the B cells are stimulated, for example, by the lymphokines secreted by T cells.

Details of the disclosure are set forth herein. Although methods and materials similar or equivalent to those described herein can be used in the practice or testing of the present disclosure, illustrative methods and materials are now described. Other features, objects, and advantages of the disclosure will be apparent from the description and from the claims.

Therapeutic Polypeptides & Corresponding Polynucleotides

*Bifidobacterium*, a commensal bacterium, has been shown to promote anti-tumor immunity and facilitate anti-programmed cell death protein ligand 1 (PD-L1) efficacy. In fact, the bacterium elicits an additive effect with anti-PD-L1 and increases MHC-II on dendritic cells. See Sivan et cd. (2015. Science. 350(6264):1084-1089).

Studies were done to identify and characterize compositions derived from *Bifidobacterium*, e.g., proteins or fragments thereof expressed by *Bifidobacterium*, which can promote activation immune cells which can facilitate destruction of tumor cells. For example, as illustrated in FIG. 1, a therapeutic composition of the present disclosure can alter the ratio of effector T cells ($T_{eff}$) to regulator T cells ($T_{reg}$). Increasing the ratio of $T_{eff}$: $T_{reg}$ cells may prevent tumor cells from escaping immune surveillance, leading to the destruction of tumor cells by the subject immune system. In some embodiments, compositions of the present disclosure can also activate dendritic cell maturation from naïve bone marrow cells, further facilitating anti-tumor activity of the subject immune system.

Accordingly, polypeptides encoded by the *Bifidobacterium* genome or fragments thereof are tested, e.g., in vitro for their ability to stimulate differentiation of naïve CD4+ and CD8+ T cells (Th0) to CD4+ and CD8+ activated T cells (Tact). For example, incubation of a naïve T cell with a *Bifidobacterium* polypeptide of interest resulting in an increase in the number of CD4+ and/or CD8+ T cells having a CD25+/FoxP3- phenotype suggests that the *Bifidobacterium* polypeptide has increased the ratio of $T_{eff}$: $T_{reg}$. Further evidence of this increased $T_{eff}$: $T_{reg}$ ratio is suggested by an increase in secretion by the treated naïve murine splenocytes of the cytokines IL-2 and IL-17, as well as the expression of granzyme B. Additionally, studies can be done to show the ability of the disclosed peptides to activate dendritic cells (DCs). Activation of DCs can be demonstrated through, e.g., increased expression of TNF, IL-1β, and/or MHC I.

Figure 2A:
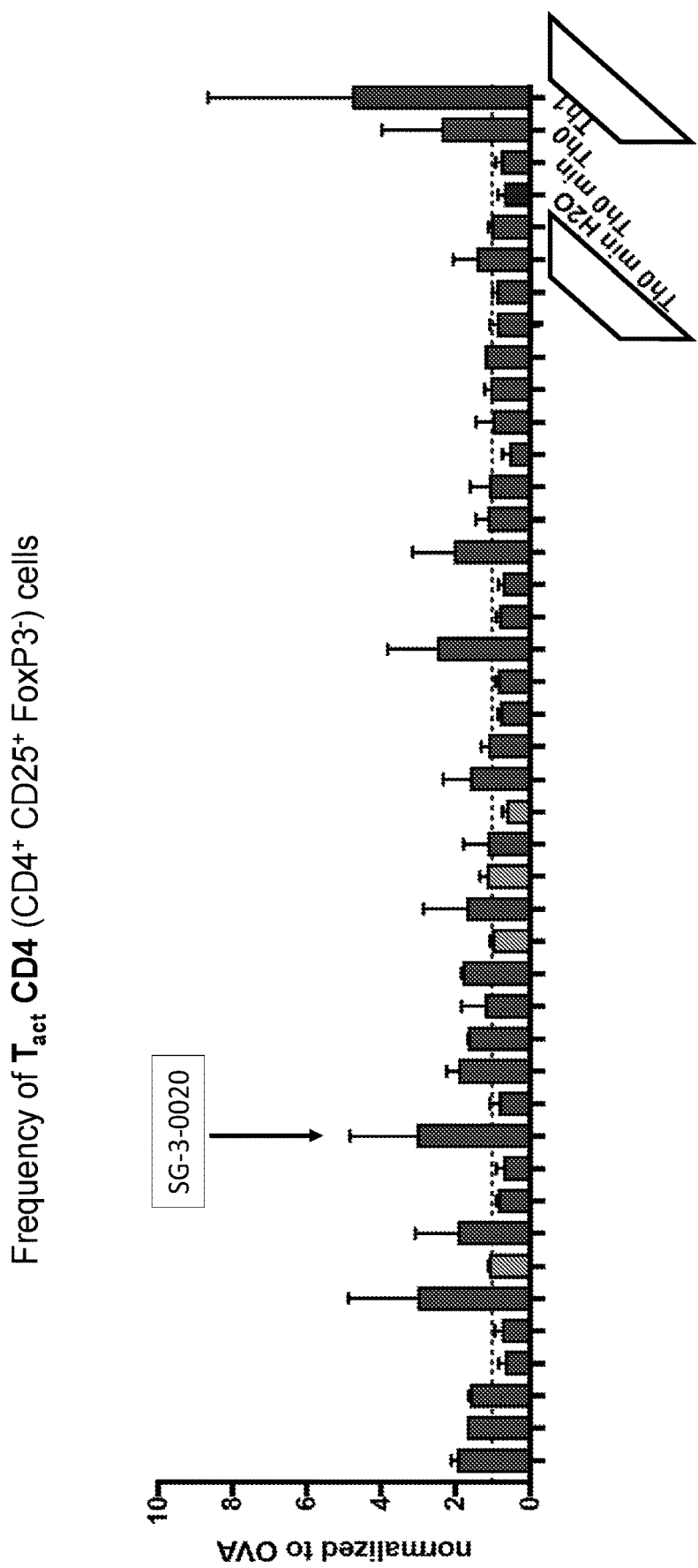
FIGS. 2A-2B show effects of peptides derived from *Bifidobacterium breve* on the frequency of CD4 (FIG. 2A) and CD8 (FIG. 2B) cells.
Figure 2B:
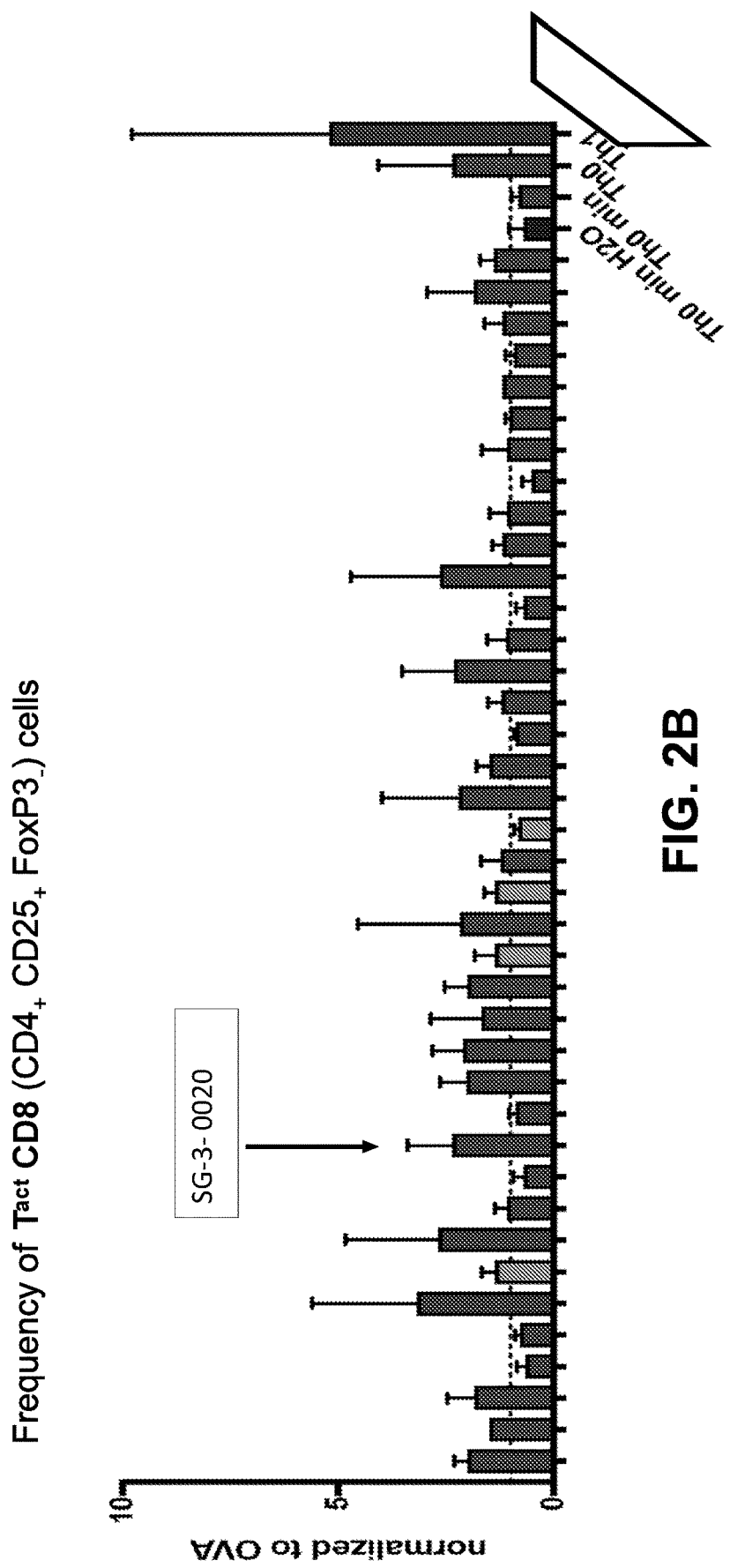

Such in vitro characterization resulted in the identification of a protein referred to herein as SG-3-0020. SG-3-0020 was shown to increase the frequency of activated CD4 and CD8 cells when incubated with splenocytes isolated from naïve mice (see Example 1 and FIGS. 2A-2B). The amino acid sequence of SG-3-0020 and its encoding nucleotide sequence is provided below in Table 1. The terms "SG-3-0020" and "SEQ ID NO:1" are used interchangeably herein.

TABLE 1

SG-3-0020 and Its Encoding Nucleic Acid Sequence

| Sequence Identifier | Amino Acid Sequence | Sequence Identifier | Encoding Nucleic Acid Sequence |
|---|---|---|---|
| SEQ ID NO: 1 | MLSTKKTKTHDHYPCGRM RDPGWHDWRACLTHQGIE EDEWPV | SEQ ID NO: 2 | ATGTTGAGTACCAAGAAGAC CAAGACCCACGACCACTACC CGTGCGGCCGCATGCGCGAC CCCGGCTGGCACGACTGGCG CGCCTGTCTCACCCACCAAG GCATCGAGGAGGATGAATGG CCGGTC |

Figures 6A, 6B:
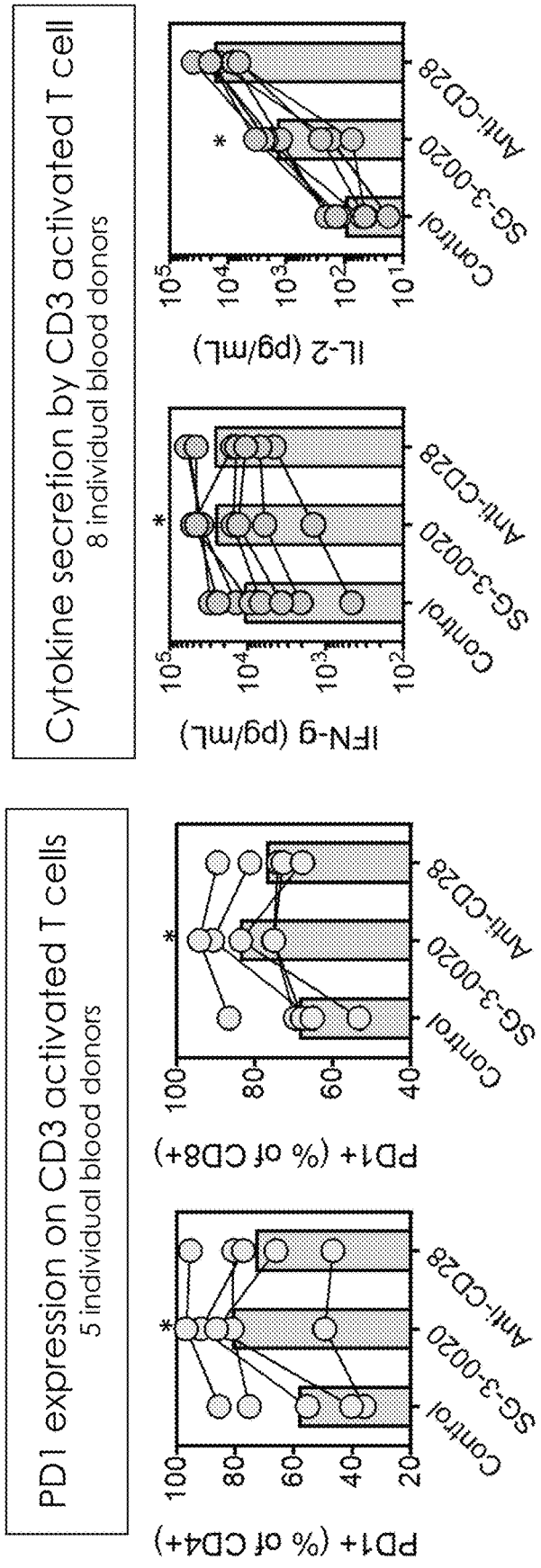
FIGS. 6A-6D show effects of a therapeutic peptide such as SG-3-0020 on activation of human T cells.
Figure 6C:
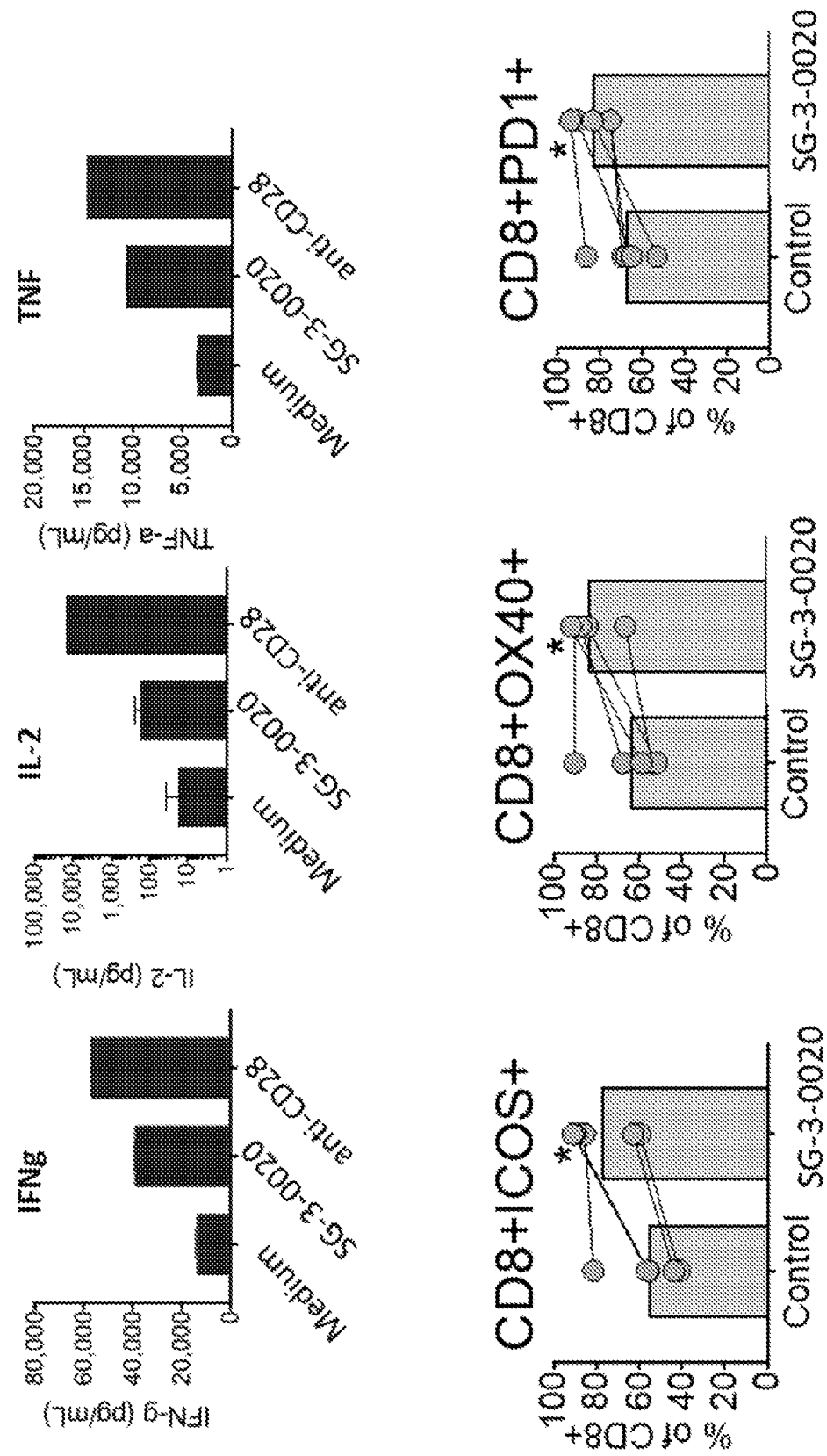
Figure 6D:
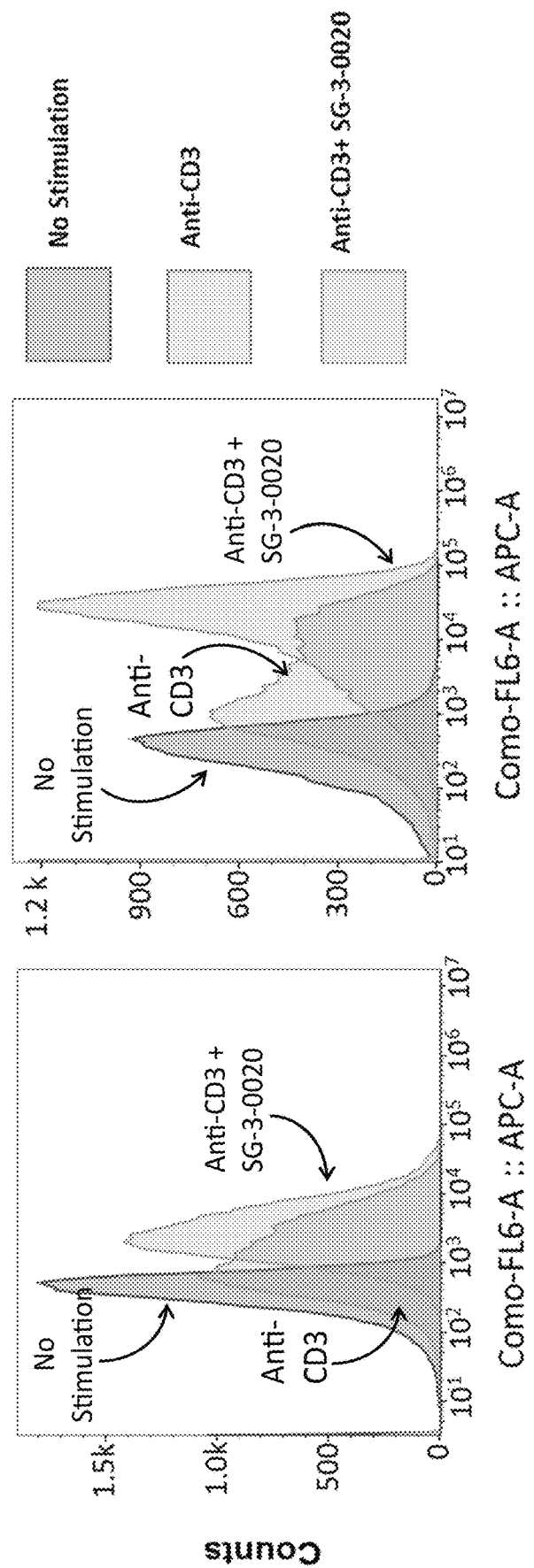
Figure 9:
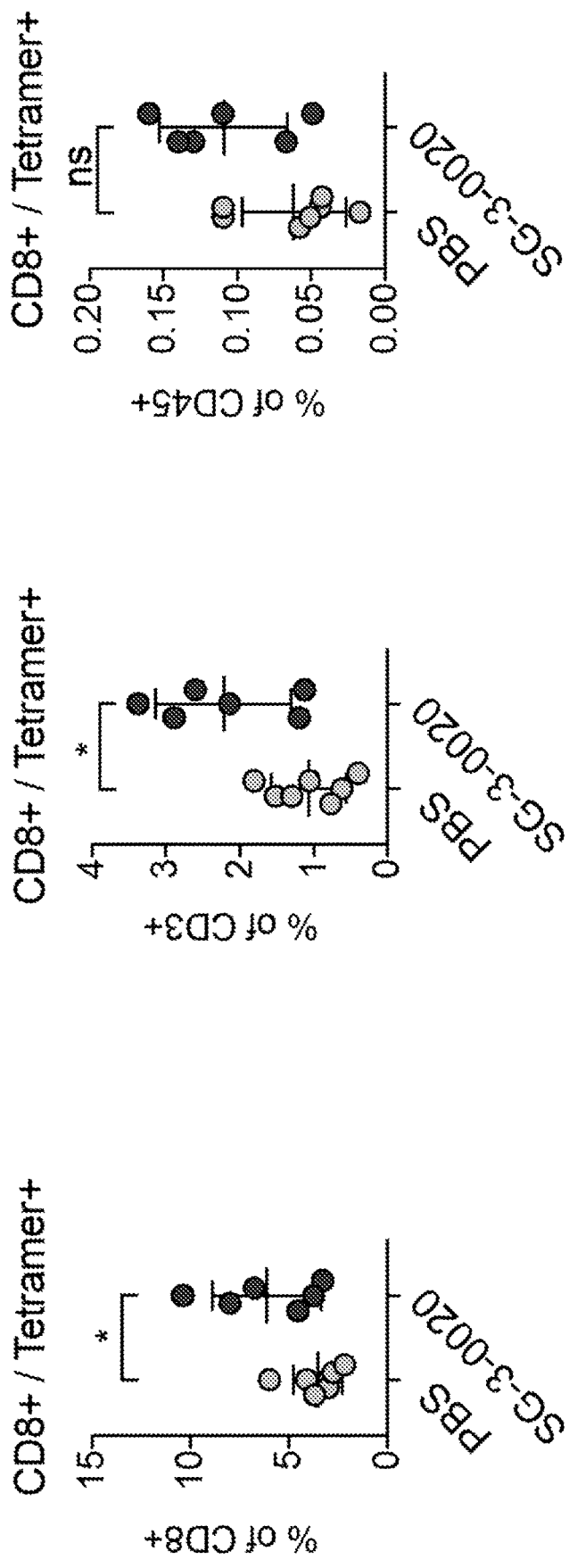

Subsequent experiments, described in Examples 2 and 3 below, show that SG-3-0020 augments activation of human T cells in vitro and increases NK cell and activated CD8+ T cell frequency within the tumor infiltrating lymphocyte (TIL) compartment (see FIGS. 6A and 6B). Specifically, SG-3-0020 was shown to affect adaptive immunity though T cell modulation. In Example 2, purified T cells obtained from 5 individual human donors were stimulated with anti-CD3 antibody and incubated with or without SG-3-0020. The presence of SG-3-0020 resulted in an increase in surface PD-1 expression in both CD4+ and CD8+ cells. Moreover, the incubation of the activated T cells with SG-3-0020 resulted in an increase in IFN-γ, IL-2, IL-10, TNF-α secretion. Also observed in the presence of SG-3-0020 (as compared to activated T cells in the absence of SG-3-0020 was an increase in T cells which were: CD4+ CD25+, CD4+ICOS+, CD4+OX40+, CD8CD25+, CD8+ ICOS+ and CD8+OX40+(data not shown).

In vivo studies were also performed and showed that peri-tumoral administration of SG-3-0020 increases immune activation in the tumor microenvironment (TME). Peri-tumoral injections twice daily (b.i.d.) resulted in an increase in NK cell and activated CD8+ T cell frequency in the TIL compartment (FIG. 7B).

The above studies show that SG-3-0020 and variants thereof having comparable biological activity are effective in modulating the immune system of a subject and can therefore be viable as a therapeutic agent for treatment of cancer and/or reduction of tumor volume and/or tumor growth.

Peptide Variants

As aforementioned, modifications and/or changes may be made in the structure of therapeutic proteins, e.g., SG-3-0020, disclosed herein. Thus, the present disclosure contemplates variation in sequence of these proteins, and nucleic acids coding therefore, where they are nonetheless able to retain substantial activity with respect to the preventative and curative aspects of the present disclosure.

A. Modified Peptides

Certain amino acids of SG-3-0020 may be substituted for other amino acids in a protein/peptide structure without appreciable loss of interactive binding capacity with structures such as, for example, antigen-binding regions of antibodies, binding sites on substrate molecules, receptors, and such like. Thus, these proteins/peptides can be biologically functional equivalents of SG-3-0020 (e.g. SEQ ID NO:1). The amino substitutions may or may not be conserved substitutions. "Conservative" changes therefore do not disrupt the biological activity of the peptide, as the structural change is not one that impinges on the protein's ability to carry out its designed function, such as a function resulting from an interaction with another moiety.

A variant of SG-3-0020 according to the present disclosure can be a protein with 1, 2, 3, 4, 5, 6, 7, 8, 9, or 10 amino acid substitutions relative to SEQ ID NO:1. Alternatively stated, the variant can be at least 75%, 80%, 85%, 90%, 91%, 92%, 93%, 94%, 95%, 96%, or 97% identical to SEQ ID NO:1. In some embodiments, a peptide of the present disclosure has a deletion of 1, 2, 3, 4 or 5 N- or C-terminal residues of SEQ ID NO:1. Alternatively or additionally, there is an internal deletion of 1, 2, 3, 4, or 5 amino acids relative to SEQ ID NO:1.

Contemplated herein are conservatively modified variants of SG-3-0020. "Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (see U.S. Pat. No. 5,767,063; Kyte and Doolittle (1982) J Mol. Biol. 157:105-132). (1) Hydrophobic: Norleucine, Ile, Val, Leu, Phe, Cys, Met; (2) Neutral hydrophilic: Cys, Ser, Thr; (3) Acidic: Asp, Glu; [0093] (4) Basic: Asn, Gln, His, Lys, Arg; (5) Residues that influence chain orientation: Gly, Pro; (6) Aromatic: Trp, Tyr, Phe; and (7) Small amino acids: Gly, Ala, Ser. Thus, the term "conservative substitution" with respect to an amino acid denotes that one or more amino acids are replaced by another, biologically similar residue, wherein said substitution does not generally affect the functional properties of the protein. In some embodiments, the disclosure provides for proteins that have at least one non-naturally occurring conservative amino acid substitution relative to the amino acid sequence identified in SEQ ID NO:1.

Also contemplated are modifications of the therapeutic protein. For example, there may be an acetyl (Ac) and/or or an amide group at the C- and/or N-terminus of the protein. In some embodiments, the protein may "cyclized," referring to a reaction in which one part of a polypeptide molecule becomes linked to another part of the polypeptide molecule to form a closed ring, such as by forming a disulfide bridge or other similar bond. The SG-3-0020 protein or variant thereof may be linked to another molecule, e.g., protein (e.g., BSA or Fc domain) or stabilizing group such as a PEG molecule, by a linker. A "linker moiety," as used herein, refers broadly to a chemical structure that is capable of linking or joining together two peptide monomer subunits to form a dimer.

In some embodiments, the peptides of the present disclosure are modified to increase the solubility of the peptide in an aqueous solution, relative to the unmodified peptide. In some embodiments, the peptides of the present disclosure are modified to decrease the solubility of the peptide in an aqueous solution, relative to the unmodified peptide. In some embodiments, the peptides of the present disclosure are modified to increase the solubility of the peptide in a polar solvent, relative to the unmodified peptide. In some embodiments, the peptides of the present disclosure are modified to decrease the solubility of the peptide in a polar solvent, relative to the unmodified peptide. In some embodiments, the peptides of the present disclosure are modified to increase the solubility of the peptide in a non-polar solvent, relative to the unmodified peptide. In some embodiments, the peptides of the present disclosure are modified to decrease the solubility of the peptide in a non-polar solvent, relative to the unmodified peptide.

In some embodiments, the peptides of the present disclosure are modified to increase the net charge of the peptide at human physiological pH, relative to the unmodified peptide at human physiological pH. In some embodiments, the peptides of the present disclosure are modified to decrease the net charge of the peptide at human physiological pH, relative to the unmodified peptide at human physiological pH.

In some embodiments, a peptide described herein can have a post-translational modification (PTM). Protein PTMs occur in vivo and can increase the functional diversity of the proteome by the covalent addition of functional groups or proteins, proteolytic cleavage of regulatory subunits or degradation of entire proteins. Isolated proteins prepared according to the present disclosure can undergo 1 or more PTMs in vivo or in vitro. The type of modification(s) depends on host cell in which the protein is expressed and includes but is not limited to phosphorylation, glycosylation, ubiquitination, nitrosylation (e.g., S-nitrosylation), methylation, acetylation (e.g., N-acetylation), lipidation (myristoylation, N-myristoylation, S-palmitoylation, farnesylation, S-prenylation, S-palmitoylation) and proteolysis may influence almost all aspects of normal cell biology and pathogenesis. The isolated and/or purified SG-3-0020 proteins or variants or fragments thereof as disclosed herein may comprise one or more the above recited post-translational modifications.

For each of the variants of SG-3-0020 described above, one having ordinary skill in the art can assess and compare the biological activity according to the assays disclosed herein (e.g., T cell activation assays or in vivo assays assessing effects on tumor volume).

Immunotherapy Using Compositions Comprising SG-3-0020 or Variants Thereof

In some embodiments, compositions comprising the polypeptides or peptides of the present disclosure (e.g., SG-3-0020 and/or variants thereof) are useful for immunotherapy in a subject in need thereof "Immunotherapy" refers to the treatment of a disease or disorder by inducing, enhancing, or suppressing an immune response in subject. Immunotherapies designed to elicit or amplify an immune response are known as activation immunotherapies. Immunotherapies designed to reduce or suppress an immune response are known as suppression immunotherapies. Successful immunotherapeutics for e.g., malignancies, autoimmune reactions, and chronic infection rely on the development of new approaches for efficient means to induce or control an immune response.

T Cells

A critical step in mounting an immune response in mammals is the activation of an appropriate set of T cells which can recognize an antigen associated with a disease or disorder. T cells can differentiate into helper, regulatory, cytotoxic or memory T cells. CD4+ and CD8+ T cells make up the majority of T cells. CD4+ helper T cells recognize MHC-II restricted exogenous antigens that have been captured and processed in the cellular endosomal pathway in antigen presenting cells, such as dendritic cells (DCs), then complexed onto the MHC-II in the Golgi compartment to form an antigen-MHC-II complex. This complex, expressed on the cell surface, can induce activation of CD4+ effector T cells.

CD4+ T cells can be activated and differentiated into distinct effector subtypes including T-helper 1 (Th1), T-helper 2 (Th2), T-helper 17 (Th17), follicular helper T cell (Tfh), induced T-regulatory cells (iTreg) and regulatory type 1 cells (Trl). CD4+ T cells (Th cells) produce interleukins which in turn help to activate other arms of the immune system. For example, Th cells produce interleukin-4 (IL-4) and IL-5, which aid B cells in producing antibodies; IL-2 which activates CD4+ and CD8+ T cells. Interleukin-12 (IL12) and interferon γ (IFNγ) are critical cytokines which initiate the downstream signaling cascade to develop Th1 cells. The IL12, in turn, induces natural killer cells (NK) to produce IFNγ. Since Th cells that recognize MHC-II restricted antigens play a central role in the activation and clonal expansion of cytotoxic T cells, macrophages, natural killer (NK) cells, and B cells, the initial event of activating the helper T cells in response to an antigen is crucial for the induction of an effective immune response directed against that antigen.

CD8+ T cells (cytotoxic T lymphocytes) are important for immune defense against intracellular pathogens and for tumor surveillance. CD8+ cells are activated when the desired protein/peptide is routed through the cell in such a manner so as to be presented on the cell surface as a processed protein/peptide, which is complexed with MHC-I antigens. CD8+ cytotoxic T cells destroy infected target cells though the release of perforin, granzymes, and granulysis.

Regulatory T cells ($T_{regs}$) function primarily to suppress potentially deleterious activities of Th cells. $T_{regs}$ may express a member of the FOX protein family, forkhead box P3 (FOXP3), which functions as a master regulator of the regulatory pathway in the development and function of regulatory T cells. $T_{regs}$ are often involved in dialing down the immune response. In the instance of cancer, an excess of $T_{reg}$ activity can prevent the immune system from destroying cancer cells.

Dendritic Cells

In addition to the critical roles that T cells play in the immune response, dendritic cells (DCs) are equally important. DCs are professional antigen-presenting cells that process antigen material and present it on the cell surface to T cells. DCs having a key regulatory role in the maintenance of tolerance to self-antigens and in the activation of innate and adaptive immunity (Banchereau et al., 1998, *Nature* 392:245-52; Steinman et al., 2003, *Annu. Rev. Immunol.* 21:685-711).

DCs are derived from hematopoietic bone marrow progenitor cells, which initially transform into immature dendritic cells. Immature dendritic cells constantly sample the surrounding environment for pathogens, which is down through pattern recognition receptors such as the toll-like receptors (TLRs). Antigen-presenting cells (APCs), such as DCs and macrophages, play important roles in the activation of innate and adaptive immunity as well as in the maintenance of immunological tolerance.

When DCs encounter pro-inflammatory stimuli such as microbial products, the maturation process of the cell is initiated by up-regulating cell surface expressed antigenic peptide-loaded MHC molecules and co-stimulatory molecules. Following maturation and homing to local lymph nodes, DCs establish contact with T cells by forming an immunological synapse, where the T cell receptor (TCR) and co-stimulatory molecules congregate in a central area surrounded by adhesion molecules (Dustin et al., 2000, Nat. Immunol. 1:23-9). Once activated in the presence of DCs, e.g., CD8+ T cells can autonomously proliferate for several generations and acquire cytotoxic function without further antigenic stimulation (Kaech et al., 2001, Nat. Immunol. 2:415-22; van Stipdonk et al., 2001, Nat. Immunol. 2:423-9). It has therefore been proposed that the level and duration of peptide-MHC complexes (signal 1) and co-stimulatory molecules (signal 2) provided by DCs are essential for determining the magnitude and fate of an antigen-specific T cell response (Lanzavecchia et al., 2001, Nat. Immunol. 2:487-92; Gett et al., 2003, Nat. Immunol. 4:355-60). DCs use TLRs, which recognize conserved microbial structures such as lipopolysaccharide (LPS), to promote DC maturation by activating the nuclear factor-κB (NF-κB) signaling pathway (Akira et al., 2004, Nat. Rev. Immunol. 4:499-51 1). Efforts to induce immunization to tumors have attempted to promote DC maturation and co-stimulation as a means of enhancing antitumor immunity.

Much attention has also been focused on pro-inflammatory signaling but less is known about the mechanisms that suppress and resolve inflammation. The magnitude and duration of TLR-initiated immune responses is dictated by the strength and duration of proinflammatory signaling and by the regulation of signal transduction pathways. Since TLR-induced activation of the transcription factor NF-κB is essential for the transcription of a large number of proinflammatory genes, multiple mechanisms are utilized to negatively regulate TLR signaling at multiple levels for the protection of subjects from excessive immune responses such as septic shock and for maintaining immune homeostasis in situations of chronic microbial exposure such as the intestinal microenvironment.

Cytokines

Cytokines are small secreted proteins released by cells that have a specific effect on the interactions and communications between cells. Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action). There are both pro-inflammatory cytokines and anti-inflammatory cytokines. Zhang et al., "Cytokines, Inflammation and Pain," Int. Anesthesiol. Clin., Vol. 45(2):27-37 (Spring 2007). Cytokines generally stimulate proliferation or differentiation of cells of the hematopoietic lineage or participate in the immune and inflammatory response mechanisms of the body.

Cytokines are critically involved in the regulation of multiple immune cell functions (Curtsinger et al., 2003, J. Exp. Med. 197:1141-51; Valenzuela et al., 2002, J. Immunol. 169:6842-9). As noted above, various immune cell phenotypes are characterized in terms of cytokines which they secrete. Cytokines are often classified as either pro- or anti-inflammatory.

The interleukins are a family of cytokines that mediate immunological responses. Central to an immune response is the T cell, which produces many cytokines and plays a role in adaptive immunity to antigens. Cytokines produced by the T cell have been classified as type 1 and type 2 (Kelso et al., 1998. Immun. Cell Biol. 76:00-317). The type 1 cytokines include IL-2, IFN-γ, LT-α, and are involved in inflammatory responses, viral immunity, intracellular parasite immunity, and allograft rejection. Type 2 cytokines include IL-4, IL-5, IL-6, IL-10, and IL-13, and are involved in humoral responses, helminth immunity, and allergic response.

Pro-Inflammatory Cytokines

Pro-inflammatory cytokines are cytokines that are important in cell signaling and promote systemic inflammation. They are produced predominantly by activated macrophages and are involved in the upregulation of inflammatory reactions. Pro-inflammatory cytokines arise from genes that code for the translation of small mediator molecules that induce a response after upregulation. Interleukin-1 (IL-1), IL-2, IL-6, IL-12, IL-17, IL-18, IL-23, CD40L, tumor necrosis factor (TNF) such as TNF-α, gamma-interferon (IFN-gamma), granulocyte-macrophage colony stimulating factor, MCP-1, TNF-related apoptosis-inducing ligand, RANK-ligand, and TALL-1/BAFF are well characterized as pro-inflammatory cytokines. Inflammation is characterized by an interplay between pro- and anti-inflammatory cytokines. In some embodiments, administration of the peptides of the present disclosure is accompanied by an increase in pro-inflammatory cytokines.

Anti-Inflammatory Cytokines

Anti-inflammatory cytokines are a series of immunoregulatory molecules that control the pro-inflammatory cytokine response. These molecules thus modulate and help to decrease the pro-inflammatory response created by pro-inflammatory cytokines. IL-4, IL-10, IL-13, IFN-α (IFN), and transforming growth factor-beta (TGF-β) are recognized as anti-inflammatory cytokines. In some embodiments, administration of the peptides of the present disclosure is accompanied by a decrease of anti-inflammatory cytokines.

It is understood that there is a strong interplay with respect to the effects of cytokines. For example, the pro-inflammatory activity of one cytokine can be attenuated or eliminated by the anti-inflammatory activity of another.

The present disclosure contemplates the polypeptides and/or other compounds or compositions thereof may be used to treat cancer and various immune-related diseases and conditions such as T cell-mediated diseases, including those characterized by infiltration of inflammatory cells into a tissue, stimulation of T cell proliferation, inhibition of T cell proliferation, increased or decreased vascular permeability, or the inhibition thereof.

Cancer

Globally suppressed T cell function has been described in many subjects with cancer to be a major hurdle for the development of clinically efficient cancer immunotherapies. The inhibition of antitumor immune responses has largely been linked to inhibitory factors present in subjects presenting with cancer. A "neoplastic disorder" is any disorder associated with cell proliferation, specifically with a neoplasm. A "neoplasm" or "neoplasia" is an abnormal mass of tissue that may be benign or malignant. Nearly all benign tumors are encapsulated and are non-invasive. In contrast, malignant tumors are almost never encapsulated and invade adjacent tissue by infiltrative destructive growth. This infiltrative growth can be followed by tumor cells implanting at sites discontinuous with the original tumor.

A neoplasm or a neoplastic disorder can be a cancer. "Cancer" as used herein refers to an uncontrolled growth of cells which interfere with the normal functioning of the bodily organs and systems. Hemopoietic cancers, such as leukemia, are able to outcompete the normal hemopoietic compartments in a subject, thereby leading to hemopoietic failure in the form of anemia, thrombocytopenia and neutropenia; ultimately causing death.

Cancers which migrate from their original location and seed vital organs can eventually lead to the death of the subject through the functional deterioration of the affected organ(s). A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function assays, chest X-rays and bone scan, in addition to the monitoring of specific symptoms.

Methods of the present disclosure may be utilized to treat or prevent neoplastic disorders in humans, including but not limited to cancers such as sarcoma, carcinoma, fibroma, leukemia, lymphoma, melanoma, myeloma, neuroblastoma, rhabdomyosarcoma, retinoblastoma, and glioma. Cancers include but are not limited to basal cell carcinoma, biliary tract cancer, bladder cancer, bone cancer, brain and central nervous system (CNS) cancer, breast cancer, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer (small cell and non-small cell), lymphoma (including Hodgkin's and non-Hodgkin's), melanoma, myeloma, neuroblastoma, oral cavity cancer (lip, tongue, mouth, and pharynx), ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, cancer of the urinary system, as well as other carcinomas and sarcomas.

"A subject having cancer" is a subject that has been diagnosed with a cancer. In some embodiments, the subject has a cancer type characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue.

Some primary tumors are not palpable and can be detected only through medical imaging techniques such as X-rays or by needle aspirations. The use of these latter techniques is more common in early detection. Molecular and phenotypic analysis of cancer cells within a tissue will usually confirm if the cancer is endogenous to the tissue or if the lesion is due to metastasis from another site.

It has been estimated that almost half of all currently diagnosed cancers will be treated with some form of cancer medicament. However, many forms of cancer, including melanoma, colorectal, prostate, endometrial, cervical, and bladder cancer do not respond well to treatment with cancer medicaments. In fact, only about 5-10 percent of cancers can be cured using cancer medicaments alone. These include some forms of leukemias and lymphomas, testicular cancer, choriocarcinoma, Wilm's tumor, Ewing's sarcoma, neuroblastoma, small-cell lung cancer, and ovarian cancer. Treatment of still other cancers, including breast cancer, requires a combination of therapy of surgery or radiotherapy in conjunction with a cancer medicament. See Bratzler and Peterson.

The tumor environment is often refractory to immunological attack. It is desirable in cancer immunotherapy to make the tumor environment less refractory so as to increase the activity of CTLs or other effector T cells within the tumor and to improve the overall efficacy of treatment. As used herein, "efficacy" refers to the ability of a chemotherapeutic and/or immunological composition or a combination treatment thereof to achieve a desired action or result.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the mixed lymphocyte reaction (MLR) have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Production or Synthesis of SG-3-0020 and Variants Thereof

The SG-3-0020 protein as well as any substitution variant thereof can be generated using recombinant techniques readily known to a person having ordinary skill in the art. For example, a polynucleotide sequence encoding the therapeutic protein, e.g., SEQ ID NO:2, can be subcloned into an expression vector, used to transform the appropriate host cell, e.g., *E. coli* BL21 cells, and the cells can be cultured to allow growth of the cells and expression of the protein. Expressed protein can then be purified, again using a variety of methods readily known to a person having ordinary skill in the art. Generally, "purified" will refer to a specific protein/peptide composition that has been subjected to fractionation to remove non-proteinaceous components and various other proteins, polypeptides, or peptides, and which composition substantially retains its activity, as may be assessed, for example, by the protein assays, as described herein below, or as would be known to one of ordinary skill in the art for the desired protein, polypeptide or peptide.

In some embodiments, the host cell can be at least one organism. In some embodiments, the organism may be, but is not limited to, a prokaryote (e.g., a eubacteria, an archaea) or a eukaryote (yeast).

Numerous cell lines and cultures are available for use as a host cell, and they can be obtained for example through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KCB, bacilli such as *Bacillus subtilis*; and other enterobacteriaceae such as *Salmonella typhimurium, Serratia marcescens*, various *Pseudomonas* species, as well as a number of commercially available bacterial hosts such as SURE® Competent Cells and SOLOPACK™ Gold Cells (STRATAGENE®, La Jolla). In some embodiments, bacterial cells such as *E. coli* are particularly contemplated as host cells.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

From a given amino acid sequence (e.g. SEQ ID NO:1), a skilled artisan would know how to take the sequence and utilize a codon optimization algorithm to generate the nucleotide sequence. The codon optimization algorithm chooses an appropriate codon for a given amino acid based on the expression host's codon usage bias. Many codon optimization algorithms also take into account other factors such as mRNA structure, host GC content, ribosomal entry sites. Some examples of codon optimization algorithms and gene synthesis service providers are: GenScript: www.genscript.com/codon-opt.html; ThermoFisher: www.thermofisher.com/us/en/home/life-science/cloning/gene-synthesis/geneart-gene-synthesis/geneoptimizer.html; and Integrated DNA Technologies: www.idtdna.com/CodonOpt. The nucleotide sequence is then synthesized and cloned into an appropriate expression vector.

Where the term "substantially purified" is used, this will refer to a composition in which the specific protein, polypeptide, or peptide forms the major component of the composition, such as constituting about 50% of the peptides in the composition or more. In preferred embodiments, a substantially purified peptide will constitute more than 60%, 70%, 80%, 90%, 95%, 99% or even more of the peptides in the composition.

A peptide, polypeptide or protein that is "purified to homogeneity," as applied to the present disclosure, means that the peptide, polypeptide or protein has a level of purity where the peptide, polypeptide or protein is substantially purified or free from other proteins/peptides and biological components. For example, a purified peptide, polypeptide or protein will often be sufficiently free of other protein/peptide components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

Although preferred for use in some embodiments, there is no general requirement that the protein, polypeptide, or peptide always be provided in their most purified state. Indeed, it is contemplated that less substantially purified protein, polypeptide or peptide, which are nonetheless enriched in the desired peptide compositions, relative to the natural state, will have utility in some embodiments.

Methods exhibiting a lower degree of relative purification may have advantages in total recovery of peptide product, or in maintaining the activity of an expressed peptide. Inactive products also have utility in some embodiments, such as, e.g., in determining antigenicity via antibody generation.

In other embodiments, a preparation enriched with the peptides may be used instead of a purified preparation. In this document, whenever purified is used, enriched may be used also. A preparation may not only be enriched by methods of purification, but also by the over-expression or over-production of the peptide by bacteria when compared to wild-type. This can be accomplished using recombinant methods, or by selecting conditions which will induce the expression of the peptide from the wild type cells.

In an alternative embodiment, the SG-3-0020 protein or variant thereof can be chemically synthesized, through methods readily known to a person having ordinary skill in the art.

Expression Systems

Provided herein are compositions and methods for producing proteins of the present disclosure as well as expression vectors which contain polynucleotide sequences encoding the proteins and host cells which harbor the expression vectors. The proteins of the present disclosure can be prepared by routine recombinant methods, e.g., culturing cells transformed or transfected with an expression vector containing a nucleic acid encoding the therapeutic protein described herein. Numerous expression systems can be used to produce a peptide as discussed above. Prokaryote- and/or eukaryote-based systems can be employed for use with the present disclosure to produce nucleic acid sequences, or their cognate polypeptides, proteins and peptides. Many such systems are commercially and widely available. Expression systems include but are not limited to insect cell/baculovirus systems and inducible mammalian expression systems, it is contemplated that the proteins, polypeptides or peptides produced by the methods of the disclosure may be "overexpressed." For example, the proteins, polypeptides or peptides can be expressed in increased levels relative to its natural expression in cells.

Accordingly, a method for producing any of the herein described proteins is further provided and comprises culturing host cells under conditions suitable for expression of the desired protein and recovering the desired protein from the cell culture. The recovered protein can then be isolated and/or purified for use in in vitro and in vivo methods, as well as for formulation into a pharmaceutically acceptable composition. In some embodiments, the protein is expressed in a prokaryotic cell such as *E. coli, Lactococcus lactis, Streptomyces* species (e.g., *S. coelicolor, S. lividans, S. albus*, or *S. venezuelae*), or *Bacillus* species (e.g., *B. subtilis*). In some embodiments, the protein is expressed in a eukaryotic cell such as a yeast (e.g., *Saccharomyces cerevisiae, Pichia pastoris, Yarrowia lipolytica, Aspergillus niger, Hansenula polymorpha*) or an insect cell (e.g., sf9, sf21, Tni, and S2). In some embodiments, the isolation and purification of the protein includes one or more steps to reduce endotoxin to levels acceptable for therapeutic use in humans or other animals.

Also provided herein are expression vectors which comprise a polynucleotide sequence which encodes a protein of the present disclosure. Polynucleotide sequences encoding the proteins of the disclosure can be obtained using standard recombinant techniques. Desired encoding polynucleotide sequences may be amplified from the genomic DNA of the source bacterium, i.e., *Bifidobacterium breve*. Alternatively, polynucleotides can be synthesized using nucleotide synthesizer. Once obtained, sequences encoding the polypeptides are inserted into a recombinant vector capable of replicating and expressing heterologous (exogenous) polynucleotides in a host cell. Many vectors that are available and known in the art can be used for the purpose of the present disclosure.

Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using a pBR322, pUC, pET or pGEX vector, a plasmid derived from an E. coli species. Such vectors contain genes encoding ampicillin (Amp) and tetracycline (Tet) resistance and thus provides easy means for identifying transformed cells. These vectors as well as their derivatives or other microbial plasmids or bacteriophage may also contain, or be modified to contain, promoters which can be used by the microbial organism for expression of endogenous proteins.

An expression vector of the present disclosure may comprise a promoter, an untranslated regulatory sequence located upstream (5') and operably linked to a protein-encoding nucleotide sequence such that the promoter regulated transcription of that coding sequence. Prokaryotic promoters typically fall into two classes, inducible and constitutive. An inducible promoter is a promoter that initiates increased levels of transcription of the encoding polynucleotide under its control in response to changes in the culture condition, e.g., the presence or absence of a nutrient or a change in temperature. A large number of promoters recognized by a variety of potential host cells are well known and a skilled artisan can choose the promoter according to desired expression levels. Promoters suitable for use with prokaryotic hosts include E. coli promoters such as lac, trp, tac, trc and ara, viral promoters recognized by E. coli such as lambda and T5 promoters, and the T7 and T7lac promoters derived from T7 bacteriophage. A host cell harboring a vector comprising a T7 promoter, e.g., is engineered to express a T7 polymerase. Such host cells include E. coli BL21(DE3), Lemo21(DE3), and NiCo21(DE3) cells. Promoters suitable for use with yeast hosts include promoters such as yeast alcohol dehydrogenase 1 (ADH1) promoter, yeast phosphoglycerate kinase (PGK1) promoter, and translational elongation factor EF-1 alpha promoter. In some embodiments, wherein the host cell is a H. polymorpha cell, the promoter is a MOX promoter. In some embodiments, the promoter is an inducible promoter which is under the control of chemical or environmental factors.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with (3-galactosidase, ubiquitin, and the like.

Suitable vectors for expression in both prokaryotic and eukaryotic host cells are known in the art.

Vectors of the present disclosure may further comprise a signal sequence which allows the translated recombinant protein to be recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. Well-known signal sequences for use in eukaryotic expression systems include but are not limited to interleukin-2, CD5, the Immunoglobulin Kappa light chain, trypsinogen, serum albumin, and prolactin.

The proteins as described herein (e.g., SG-3-0020) can be expressed as a fusion protein or polypeptide. Commonly used fusion partners include but are not limited to human serum albumin and the crystallizable fragment, or constant domain of IgG, Fc. The histidine tag or FLAG tag can also be used to simplify purification of recombinant protein from the expression media or recombinant cell lysate. The fusion partners can be fused to the N- and/or C-terminus of the protein of interest.

Methods are well known for introducing recombinant DNA, i.e., an expression vector, into a host cell so that the DNA is replicable, either as an extrachromosomal element or as a chromosomal integrant, thereby generating a host cell which harbors the expression vector of interest. Methods of transfection are known to the ordinarily skilled artisan, for example, by $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. General aspects of mammalian cell host system transformations have been described in U.S. Pat. No. 4,399,216. Transformations into yeast are can be carried out according to the method of Van Solingen et al., J. Bact, 130:946 (1977) and Hsiao et al., Proc. Natl. Acad. Sci. (USA), 76:3829 (1979). Other methods for introducing DNA into cells include nuclear microinjection, electroporation, bacterial protoplast fusion with intact cells, or introduction using polycations, e.g., polybrene, polyornithine. For various techniques for transforming mammalian cells, see Keown et al., Methods in Enzymology. 185:527-537 (1990) and Mansour et al., Nature, 336:348-352 (1988).

Accordingly, provided herein is a recombinant vector or expression vector as described above and comprising a polynucleotide which encodes a therapeutic protein sequence of interest (e.g., SEQ ID NO:1). The polynucleotide can be SEQ ID NO:2. Moreover, the present disclosure provides a host cell harboring the vector. The host cell can be a eukaryotic or prokaryotic cell as detailed above. In some embodiments, the host cell is a prokaryotic cell. In some embodiments, the host cell is E. coli, L. lactis, S. coelicolor, S. lividans, S. albus, S. venezuelae, or B. subtilis.

Pharmaceutical Compositions Comprising Therapeutic Peptides

Compositions are provided, which comprise a peptide as described herein. In embodiments, the compositions described herein are pharmaceutical compositions that are suitable for human administration, and which demonstrate a therapeutic effect when administered to a human in need thereof. Pharmaceutical compositions of the present disclosure may comprise a therapeutically effective amount of a therapeutic peptide in a pharmaceutically acceptable carrier.

The phrases "pharmaceutical or pharmacologically acceptable" refers to molecular entities and compositions suitable for administration to an animal, such as, for example, a human, as appropriate. The preparation of a pharmaceutical composition or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compositions of the disclosure may comprise different types of carriers depending on whether it is to be administered in solid, liquid or aerosol form, and whether it need to be sterile for such routes of administration as injection. The peptides of the disclosure can be administered orally, or rectally, but may also be administered intrathecally, intranasally, subcutaneously, mucosally, by inhalation (e.g., aerosol inhalation), by injection, by infusion or continuous infusion, topically, localized perfusion bathing target cells directly, via a catheter, via a lavage, or by other method or any combination of the foregoing as would be known to one of ordinary skill in the art (see, for example, Remington's Pharmaceutical Sciences, 18th Ed. Mack Printing Company, 1990, incorporated herein by reference).

The peptides of the present disclosure may be formulated into a composition in a free base, neutral, or salt form. Pharmaceutically acceptable salts, include the acid addition salts, e.g., those formed with the free amino groups of a proteinaceous composition, or which are formed with inorganic acids such as, for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In particular embodiments, the peptide compositions of the present disclosure are prepared for administration by such routes as oral ingestion. In these embodiments, the solid composition may comprise, for example, solutions, suspensions, emulsions, tablets, pills, capsules (e.g., hard or soft shelled gelatin capsules), delayed release capsules, sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

In some embodiments, an oral composition may comprise one or more binders, excipients, disintegration agents, lubricants, flavoring agents, and combinations thereof. In some embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum. After insertion, suppositories soften, melt or dissolve in the cavity. In general, for suppositories, traditional carriers may include, for example, polyalkylene glycols, triglycerides or combinations thereof. In some embodiments, suppositories may be formed from mixtures containing, for example, the active ingredient in the range of about 0.5% to about 10%, and preferably about 1% to about 2%.

In some embodiments, compositions suitable for parenteral administration are provided. Injectable formulations comprise one or more described compounds in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, amino acids, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate.

These pharmaceutical compositions may also contain adjuvants such as preservatives, wetting agents, emulsifying agents and dispersing agents. Prevention of the action of microorganisms upon the described compounds may be ensured by the inclusion of various antibacterial and antifungal agents, for example, paraben, chlorobutanol, phenol sorbic acid, and the like. It may also be desirable to include agents to control tonicity, such as sugars, sodium chloride, and the like into the compositions. In addition, prolonged absorption of the injectable pharmaceutical form may be brought about by the inclusion of agents which delay absorption such as aluminum monostearate and gelatin.

Sterile injectable solutions are prepared by incorporating the active compounds in the required amount in the appropriate solvent with various combinations of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein/peptide.

In some embodiments, the composition comprises a purified peptide that comprises, consists of, or consists essentially of, the amino acid sequence depicted in SEQ ID NO:1 or variant thereof as described above.

Combination Therapies Comprising Therapeutic Peptides

The pharmaceutical compositions provided herein comprising a therapeutic peptide may be combined with other treatment therapies and/or pharmaceutical compositions. For example, a subject suffering from an immunological associated disease or disorder, or cancer, may already be taking a pharmaceutical prescribed by their doctor to treat the condition. In embodiments, the pharmaceutical compositions provided herein, are able to be administered in conjunction with the subject's existing medicines.

For example, the therapeutic peptides provided herein may be combined with one or more of: a 5-aminosalicylic acid compound, an anti-inflammatory agent, an antibiotic, an antibody (e.g. antibodies targeting an inflammatory cytokine, e.g. antibodies targeting TNF-α, such as adalimumab, pegol, golimumab, infliximab, and certolizumab), an anti-cytokine agent, an anti-inflammatory cytokine agent, a steroid, a corticosteroid, an immunosuppressant (e.g. azathioprine and mercaptopurine), vitamins, and/or specialized diet. In some embodiments, the therapeutic peptide of the present disclosure is administered with a checkpoint inhibitor, such as an agent that targets PD-1, PD-L1, CTLA-4, BTLA, LAG-3, A2AR, TIM-3, B7-H3, VISTA, or IDO. Such drugs include but are not limited to pembrolizumab, nivolumab, atezolizumab, avelumab, durvalumab, cemiplimab, and ipilimumab. The therapeutic peptides provided herein may be combined with an autologous cellular immunotherapy (e.g., sipuleucel-T),In some embodiments, the other treatment therapies and/or pharmaceutical compositions may be selected from cancer immunotherapies such as monoclonal antibodies that activate NK cells and enhance antibody-dependent cellular cytotoxicity; cancer vaccines with or without adjuvants that stimulate a cancer-antigen-specific humoral immune response; chemotherapeutic agents such as carboplatin and/or mitotane; hormones such as adrenocorticosteroids or fluoxymesterone; or biological response modifiers that alter a subject's response to cancer rather than by direct cytotoxicity of cancer cells, such as erythropoietin or GM-CSF. An extensive, but non-limiting list of treatment therapies, pharmaceutical compositions/medicaments are disclosed in Bratzler and Peterson In some embodiments, a synergistic effect is achieved upon combining the disclosed therapeutic peptides with one or more additional therapeutic agents.

In some embodiments, one or more tumors or neoplastic tissues are debulked prior to or during immunotherapy. In some embodiments, debulking one or more tumors prior to or during immunotherapy results in either a slowing or a halt of disease progression. In some embodiments, debulking one or more tumors prior to or during immunotherapy results in tumor regression or elimination.

In some embodiments, a slowing of disease progression comprises at least a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decrease in the rate of growth or expansion of the tumor.

In some embodiments, tumor regression comprises at least a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decrease in the tumor numbers, tumor size, or tumor volume.

Any procedure that allows an assessment of the tumor or lesion size can be used. Non-limiting examples include digital rectal exam, an endoscopy (e.g., a colonoscopy), and imaging (e.g., PET, MRI, ERUS, DRE, CT). See, for example, McKeown et al. *J Cancer.* 2014; 5(1): 31-43. In some embodiments, tumor burden can be assessed using RECIST (e.g., RECIST version 1 or version 1.1). See, for example, Eisenhauer et al., *Eur. J. Cancer.* 45(2):228-47 (2009).

Criteria for evaluating immunotherapy have also been developed. Non-limiting examples include the immune-related response criteria (irRC) (see Wolchok et al. *Clin Cancer Res.* 2009 Dec. 1; 15(23):7412-20) and immune response criteria in solid tumors (iRECIST) criteria (see Seymour et al. Lancet Oncol. 2017 March; 18(3): e143-e152). See also, Thallinger et al. *Wien Klin Wochenschr.* 2018; 130(3): 85-91.

Having an antigen-specific humoral and cell-mediated immune response, in addition to activating NK cells and endogenous dendritic cells, and increasing IFN levels, can be helpful for treating cancer. Some cancer cells are antigenic and thus can be targeted by the immune system. In one aspect, peptides of the present disclosure, or peptides of the present disclosure plus one or more cancer medicaments are particularly useful for stimulating an immune response against a cancer. A "cancer antigen" as used herein is a compound, such as a peptide, associated with a tumor or cancer cell surface and which is capable of provoking an immune response when expressed on the surface of an antigen presenting cell, such as a dendritic cell. In some aspects, the antigen is presented on an APC via an MHC molecule. Cancer antigens, such as those present in cancer vaccines or those used to prepare cancer immunotherapies, can be prepared from crude cancer cell extracts or by partially purifying the antigens, using recombinant technology or de novo synthesis of known antigens. In some aspects, proteins isolated from other organisms or synthetic proteins sharing a degree of homology to said proteins are used to prepare cancer immunotherapies.

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen dependent nor MHC restricted once activated. Activated macrophages are thought to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK, CTLs, LAK, and macrophages.

The use of peptides of the present disclosure in conjunction with cancer vaccines provides an improved antigen-specific humoral and cell-mediated immune response, in addition to activating NK cells and endogenous dendritic cells, and increasing IFN levels. Such an enhancement can allow for the use of a vaccine with a reduced antigen dose to achieve the same beneficial effect.

Methods of Treatment Utilizing the Therapeutic Peptides

Methods are provided for treating, preventing, or ameliorating at least one symptom of a disease or condition, including: administering a therapeutically or prophylactically effective amount of a peptide as described herein to a subject in need thereof, i.e., a subject suffering from, or at risk of developing the disease or condition, or at least one symptom of the disease or condition.

Administration of the peptide can prevent, reduce the severity of, or eliminate at least one symptom, of the disease or condition in the subject. The subject may be an animal. The subject may be a mammal. The subject may be a human subject.

In some embodiments, the disease or condition is cancer, e.g., any of the cancers described herein. In some embodiments, the disease or condition is autoimmune thyroiditis. In some embodiments, the disease or conditions is Hodgkin's lymphoma.

In some embodiments of the methods provided herein, the pharmaceutical composition comprising a therapeutic peptide is formulated for administration to the gastrointestinal lumen, or for delayed release in the intestine, terminal ileum, or colon. In some embodiments of the methods provided herein, the pharmaceutical composition comprising a therapeutic peptide is formulated with an enteric coating.

In some embodiments of the methods provided herein, the pharmaceutical composition comprising a therapeutic peptide can treat cancer in a subject administered the composition. In some embodiments of the methods provided herein, the pharmaceutical composition comprising a therapeutic peptide can result in the induction or an increase in the production of at least one pro-inflammatory cytokine (e.g., TNF-α and/or IL-23) by an immune cell in a subject administered the composition. In some embodiments of the methods provided herein, the pharmaceutical composition comprising a therapeutic peptide can suppress at least one anti-inflammatory cytokine (e.g., IL-10) by an immune cell in a subject administered the composition.

In some embodiments of the methods herein, a second therapeutic or prophylactic agent is administered in conjunction with the peptide described herein, either simultaneously or sequentially. In some embodiments, the peptide and the second agent act synergistically for treatment or prevention of the disease, or condition, or symptom. In other embodiments, the peptide and the second agent act additively for treatment or prevention of the disease, or condition, or symptom.

Clinical Parameters for Treating Neoplasia

The administration of a composition comprising a peptide of the present disclosure results in a biological response in the subject/subject's cells. In some embodiments, administration of one or more peptides of the present disclosure results in the subject or the cells isolated therefrom to exhibit one or more of a reduction in the expression of IL-10, an increase of inflammatory (pro-inflammatory) cytokines, an increase of TNF-α, a reduction in anti-inflammatory cytokines, a limiting of tolerogenic dendritic cell expansion, a reduction in the ratio of IL-10:TNF, increase in the expression of IL-12, an increase or promotion of Th1 activation, an increase in TNF, an increase or enhancement of dendritic cell maturation, an increase in CD70 expression, an increase in T-cell activation, an increase in T-cell activation along with co-stimulation via CD27, an increase in the expression of CD80 and/or CD86, an increase or the enhancement of T-cell activation, an increase in T-cell activation along with co-stimulation via CD28, an increase in the expression of MHC I and/or MHC II, an increase or enhancement of T-cell activation by means of an increase in MHC-involved antigen presentation, a decrease in the number of $T_{reg}$ cells, preventing the clonal expansion of $T_{reg}$ cells and/or promoting the clonal expansion of $T_{eff}$ cells, an increase in the number of $T_{act}$ cells, an increase in the number of CTL cells, a decrease in the size and/or volume of neoplastic tissue, preventing metastasis of neoplastic tissue or cells, induction of apoptosis in neoplastic cells, an increase in the rate of apoptosis of neoplastic cells, a reduction in the number of neoplastic masses in one or more tissues, a decrease in the size of neoplastic lesions, and an increase in the clonal expansion of $T_{act}$, $T_{eff/mem}$, and/or CTL cells. In some embodiments, administration of one or more peptides of the present disclosure to a subject results in a decrease in expression of one or more genes selected from the group consisting of:

signal transducer and activator of transcription 1 (STAT1), interferon regulatory factor 1 (IRF1), cluster of differentiation 96 (CD96), mothers against decapentaplegic homolog 3 (SMAD3), C-X-C motif chemokine receptor 6 (CXCR6), transcription factor 7 (TCF7), lymphocyte antigen 9 (LY9), C-X-C motif chemokine 10 (CXCL10), granzyme K (GZMK), interferon stimulated exonuclease gene 20 (ISG20), and signaling lymphocytic activation molecule F7 (SLAMF7) in the subject (e.g., in cells such as T cells of the subject). In some embodiments, administration of one or more peptides of the present disclosure to a subject results in an increase in expression of one more genes selected from the group consisting of: dual specificity phosphatase 6 (DUSP6), cathepsin L (CTSL), IL-9, IL-2, IL-10, IL-24, IL-21, and IL-3 in the subject (e.g., in cells such as T cells of the subject).

In some embodiments, administration of one or more peptides of the present disclosure to a subject results in an increase in expression of one more genes selected from the group consisting of: DUSP6, CTSL, IL-9, IL-2, IL-10, IL-24, IL-21, and IL-3 in the plasma of the subject.

In some embodiments, administration of a composition comprising the peptide to a subject results in an increased life expectancy in the subject of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. In some embodiments, administration of a composition comprising the peptide to a subject results in an increased life expectancy in the subject of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In some embodiments, administration of a composition comprising the peptide to a subject results in an increased life expectancy in the subject of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 years.

In some embodiments, administration to a subject of a composition comprising the peptide results in a reduction in the volume of one or more neoplasia by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 98% of the volume of the one or more neoplasia.

In some embodiments, administration to a subject of a composition comprising the peptide results in a reduction of the size of one or more neoplastic lesions by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 98% of the volume of the one or more neoplastic lesions.

In some embodiments, administration to a subject of a composition comprising the peptide results in a reduction in one or more negative side effects of the neoplasia by at least 5%, 10%, 20%, 25%, 30%, 35%, 40%, 45%, 50%, 55%, 60%, 65%, 70%, 75%, 80%, 85%, 90%, or 95%; wherein the negative side effects include nausea, pain, discomfort, vomiting, diarrhea, vertigo, loss of appetite, nerve pain, seizures, periodic loss of consciousness, loss or lack of ambulatory movement, loss or lack of physical coordination, and loss or lack of vision.

In some embodiments, administration to a subject of a composition comprising the peptide results in a shift in the clonal populations of $T_{reg}$ and $T_{eff}$ cells in contact with the one or more neoplasia, wherein the population of $T_{eff}$ increases at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30-fold relative to the population of $T_{reg}$.

Microbial Cultures

Methods are provided for producing the peptides described herein. The methods include culturing a host cell as described above, under conditions in which the peptide is expressed from the exogenous polynucleotide that encodes it.

*Bifidobacterium breve* (ATCC 15700) is the origin of SEQ ID NO:2, which encodes SEQ ID NO:1. The SG-3-0020 protein having the sequence of SEQ ID NO:1 was chemically synthesized according to routine equipment and methods of peptide synthesis for use in the Examples below.

The following examples are intended to illustrate, but not limit, the disclosure.

EXAMPLES

Example 1. Effect of SG-3-0020 on the Stimulation of Murine Naïve Splenocytes

Figure 2C:
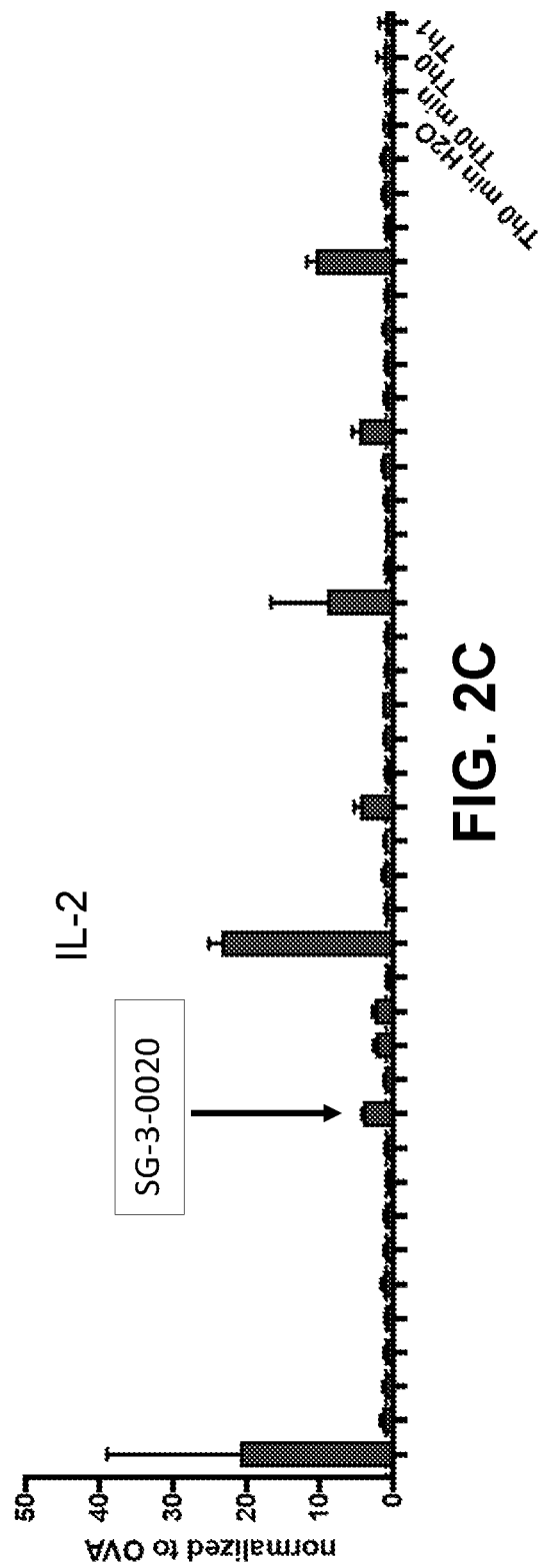
FIGS. 2C-2D show effects of peptides derived from *Bifidobacterium breve* on the secretion of IL-2 (FIG. 2C) and IL-17 (FIG. 2D) cells.

This example describes an initial screening assay to identify *Bifidobacterium*-derived peptides which can activate effector T cells, specifically, CD4 effector T cells which are characterized in part by a CD4+ CD25+ FoxP3− phenotype and CD8 effector cells which are characterized in part by a CD8+ CD25+ FoxP3− phenotype. Splenocytes isolated from naive male C57BL/6 mice (Taconic, 8-14 weeks of age) were resuspended in complete RPMI (RPMI containing 10% FBS plus 1% penicillin/streptomycin) to a final number of $8 \times 10^5$ cells/well in a flat-bottom 96-well plate. Cells were then stimulated with 0.05 μg/ml anti-CD3 antibody in the presence of: each peptide (10 μM in water) or ovalbumin peptide amino acids 323-339 (10 μM in water), water (Th0 min $H_2O$), anti-CD3 antibody alone (Th0 min), or with 1 μg/ml anti-CD3, plus IL-12 (10 ng/ml), plus 5 μg/ml anti-IL-4 antibody (positive control to generate Th1 cells). Cells were incubated at 37° C., 5% $CO_2$ for 48 h. See FIG. 2A, FIG. 2B, and FIG. 2C.

Figure 2D:
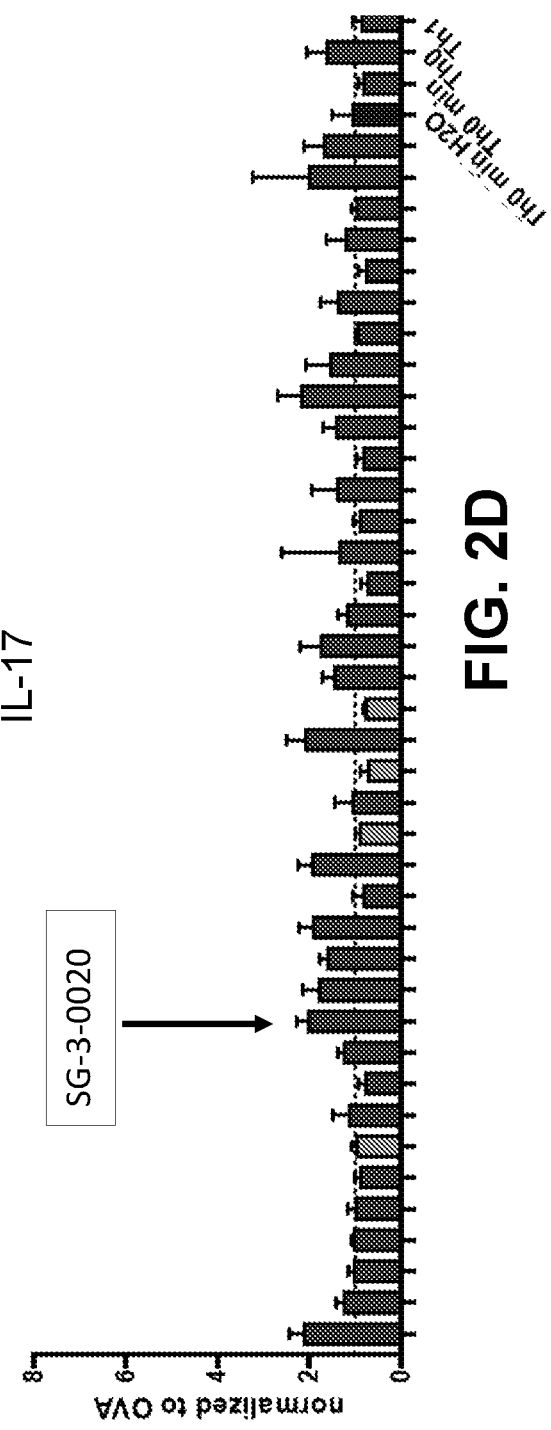
Figure 2E:
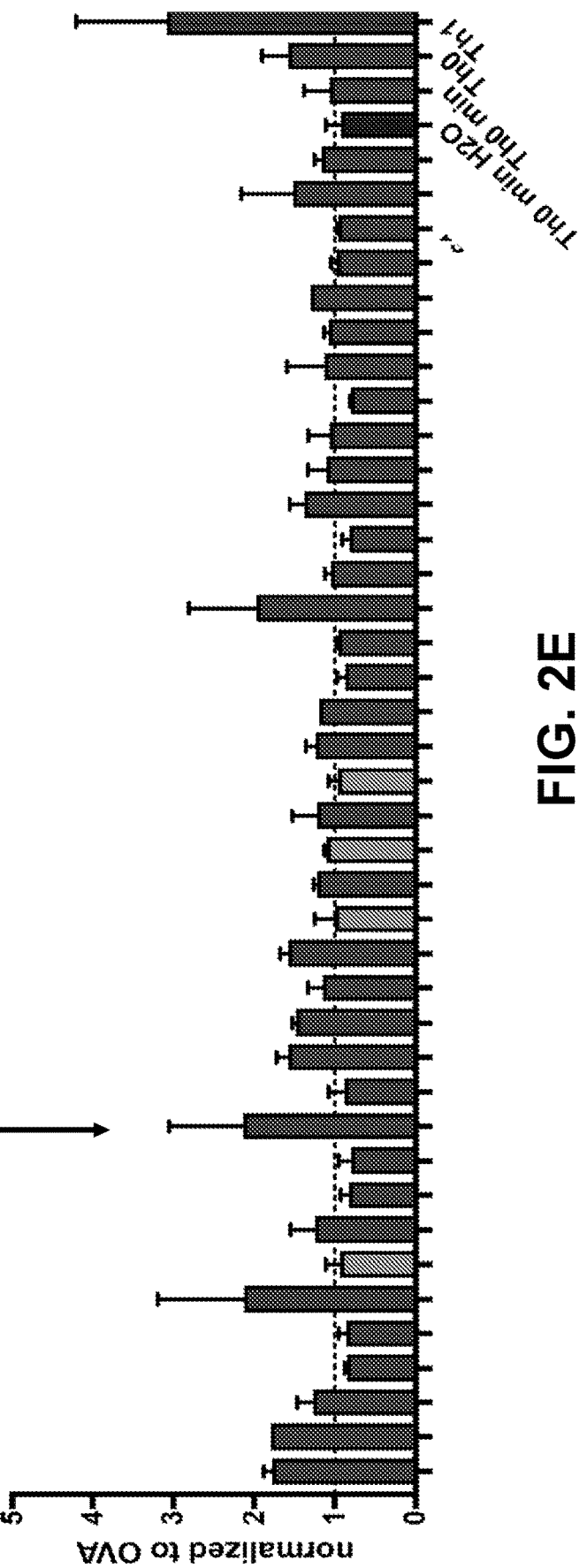
FIG. 2E shows effects of peptides derived from *Bifidobacterium breve* on the expression of Granzyme B on CD8 cells.

Levels of activated ($T_{act}$) CD4 (FIG. 2A) and CD8 (FIG. 2B) T cells, defined by absence of FoxP3 and high CD25 expression, were determined by multicolor flow cytometry. Levels of T cells were then normalized to levels of the T cells when the splenocytes were treated with the $OV_{323-339}$ negative control peptide. See Levels of IL-2 (FIG. 2C) and IL-17 (FIG. 2D) in culture supernatants were quantified by Luminex analysis. Levels of Granzyme B expression on gated CD8 FoxP3− T cells were analyzed by flow cytometry. See FIG. 2E. Bars represent mean±SD. (vs. Th0+$H_2O$) by Kruskall-Wallis with uncorrected Dunn's test.

The ability of *Bifidobacterium*-derived SG-3-0020 to enhance in vitro expression of a cell surface marker profile (CD25+/FoxP3-) associated with CD4+ and CD8+ T cell activation (FIG. 2A and FIG. 2B), facilitate T effector cell cytokine secretion (IL-2 and IL-17) (FIG. 2C and FIG. 2D), and promote induction of a key effector molecule (Granzyme B) in CD8 T cells (FIG. 2E), suggests that SG-3-0020 or variants thereof can promote expansion or increased activity of T cells that can in turn facilitate tumor cell killing.

Figure 3A:
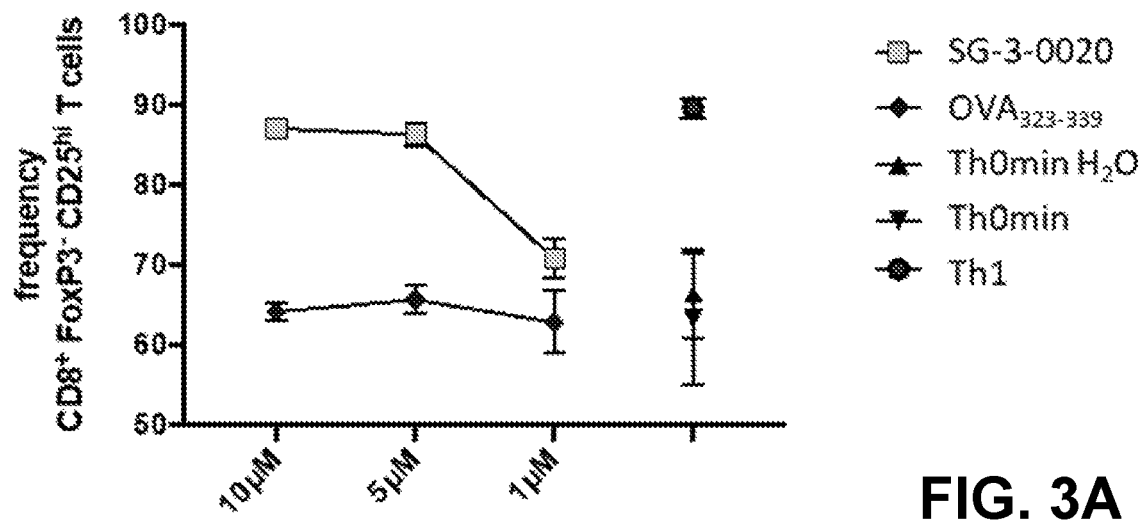
FIGS. 3A-3C show effects of a therapeutic peptide such as SG-3-0020 on frequency of Tact CD8 cells (FIG. 3A), Granzyme B expression by CD8 cells (FIG. 3B) and secretion of IL-2 (FIG. 3C).
Figure 3B:
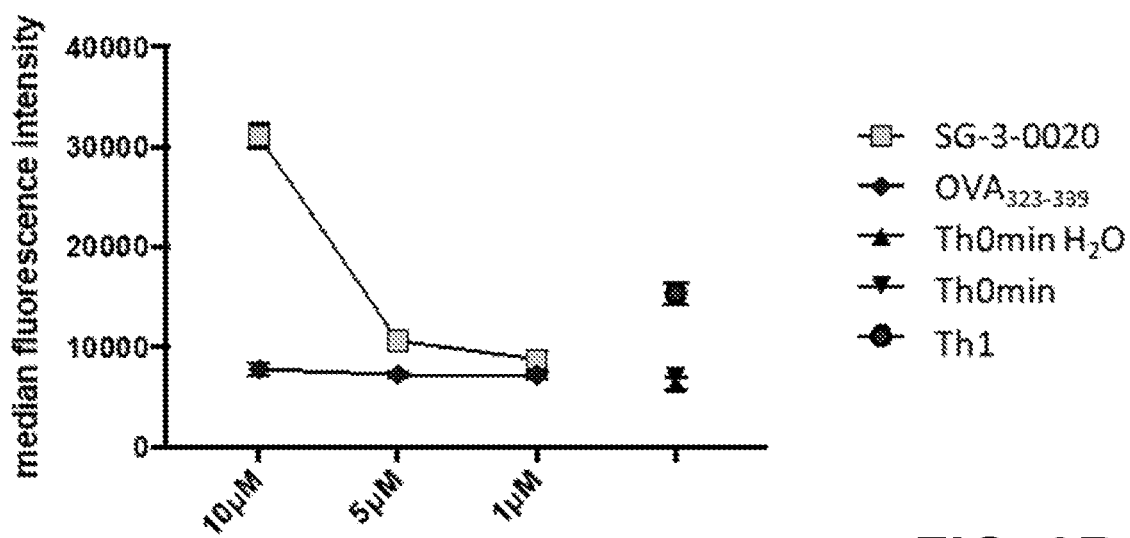
Figure 3C:
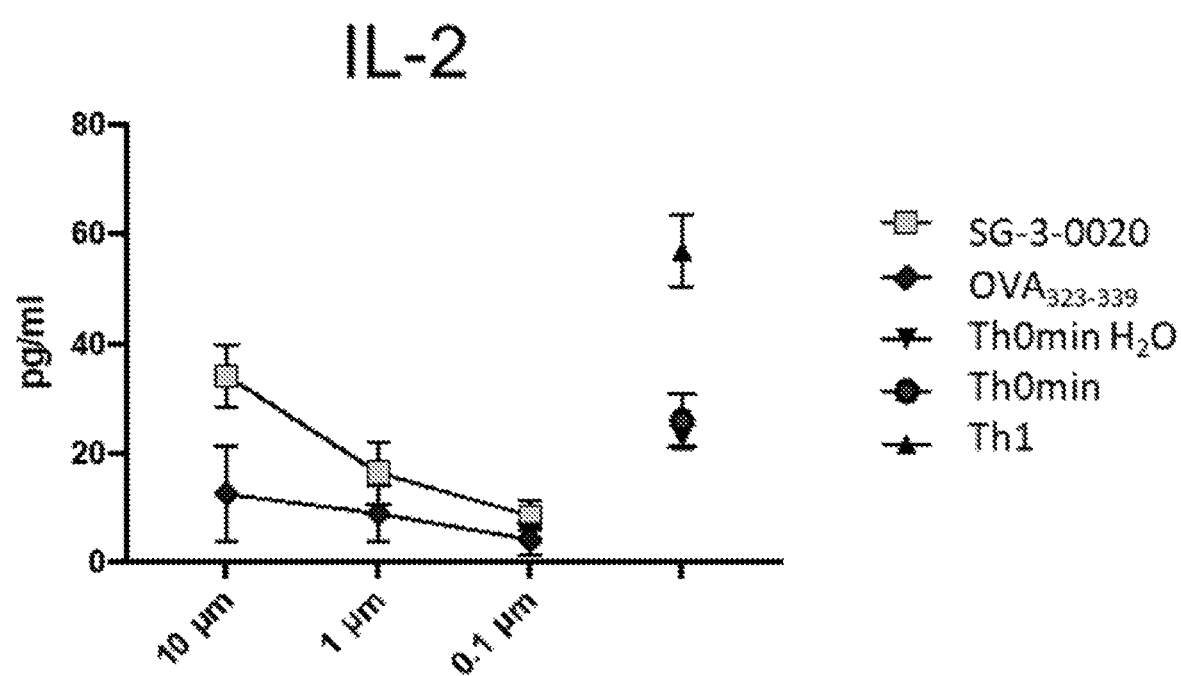

A dose response study was also performed using the above methods wherein naïve mouse splenocytes were treated with increasing doses of SG-3-0020 (1 µM, 5 µM, or 10 µM). Flow cytometry analysis was done to measure frequency of effector CD8 T cells (CD8$^+$, CD25$^+$, FoxP3), granzyme B expression on the effector CD8 T cells, and IL-2 expression. As shown in FIG. 3A, FIG. 3B, and FIG. 3C, a dose response of SG-3-0020 was observed, supporting use of SG-3-0020 as an active immunomodulating agent that can facilitate expansion or increased activity of T cells that can in turn facilitate tumor cell killing.

Example 2. Effect of SG-3-0020 on Human T Cell Activation

Figure 4:
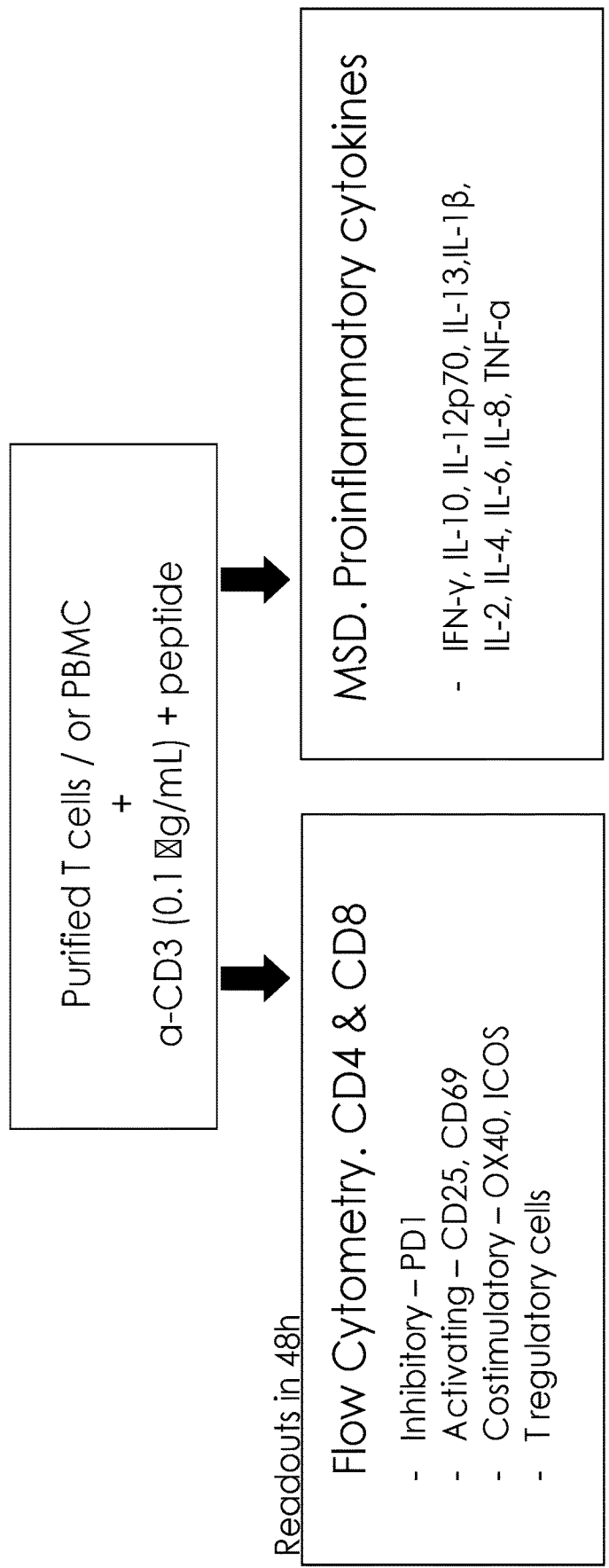
FIG. 4 is a schematic for a human T cell activation assay.
Figure 12A:
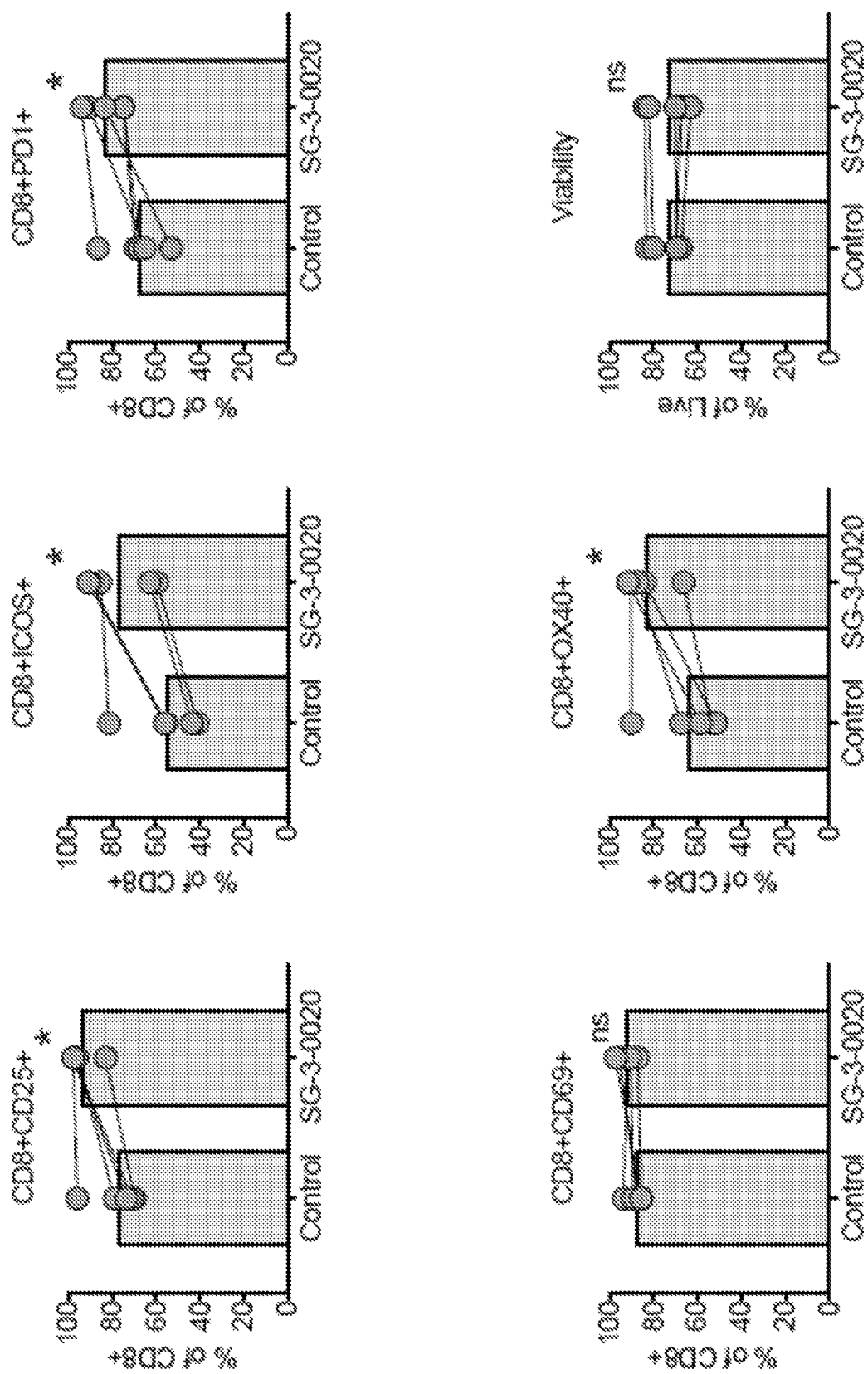
FIGS. 12A and 12B show effects of a therapeutic peptide such as SG-3-0020 on activation of human T cells.
Figure 12B:
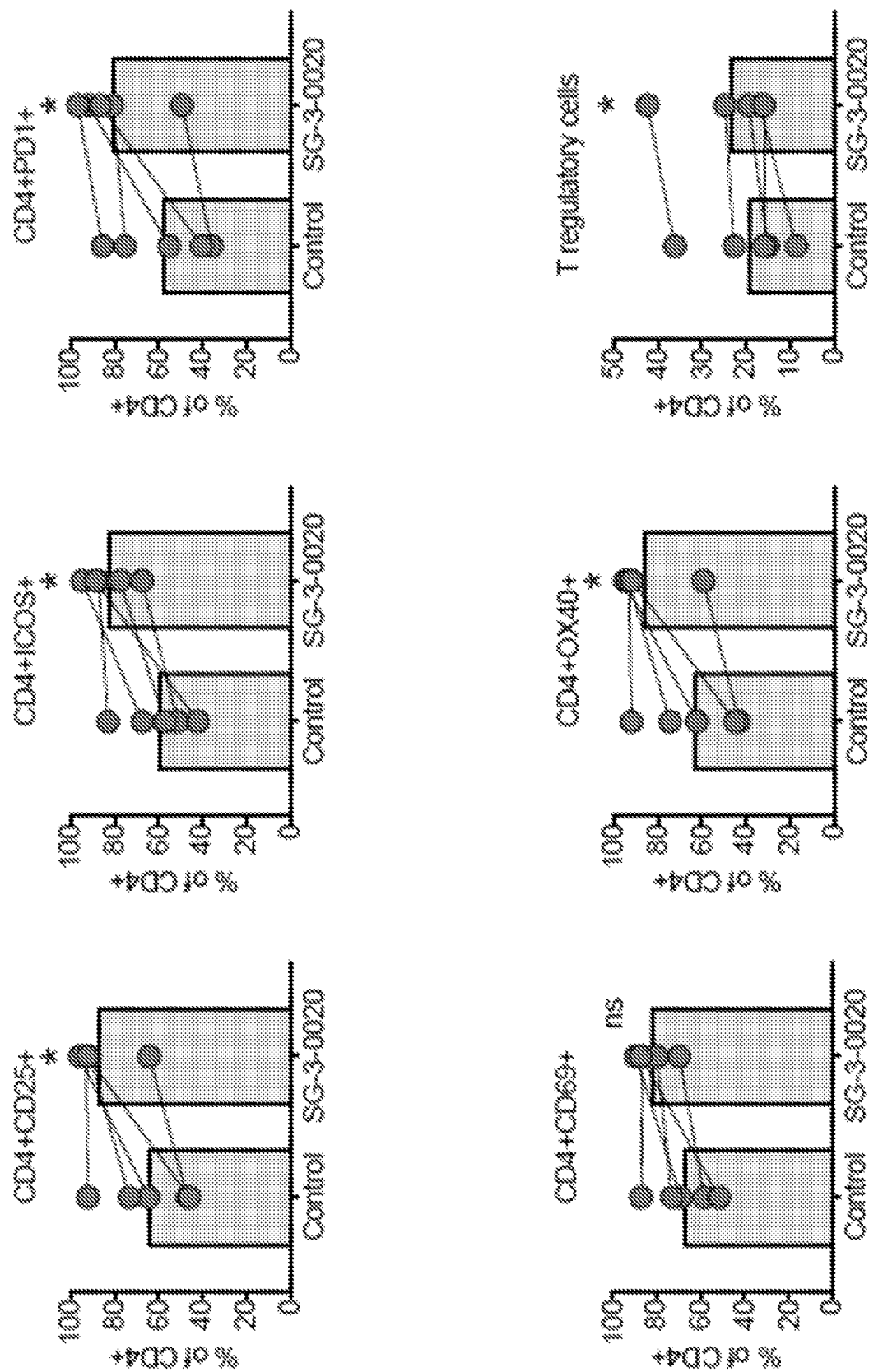
Figure 13A:
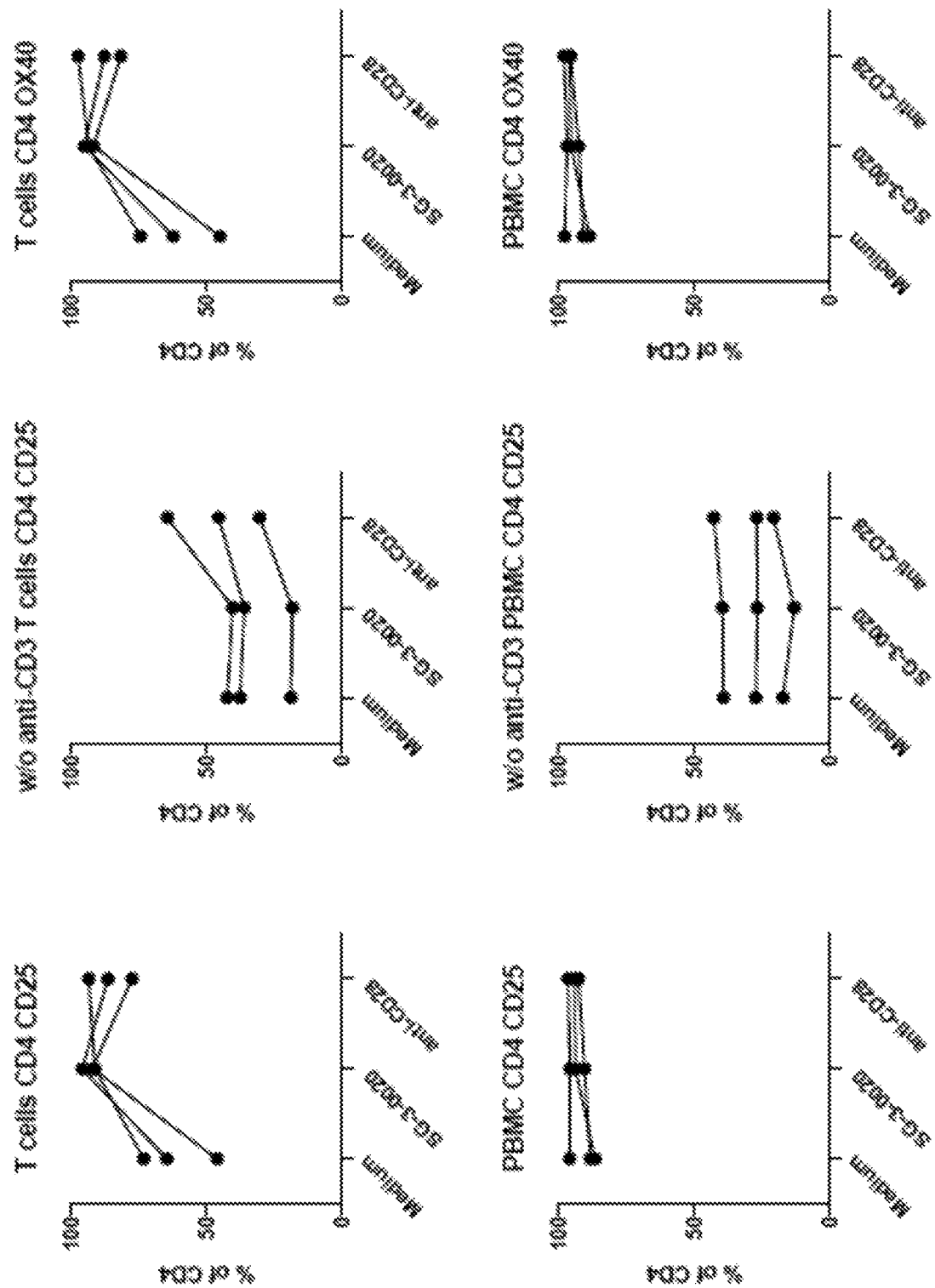
FIGS. 13A-13D shows shows effects of a therapeutic peptide such as SG-3-0020 on activation markers.
Figure 13B:
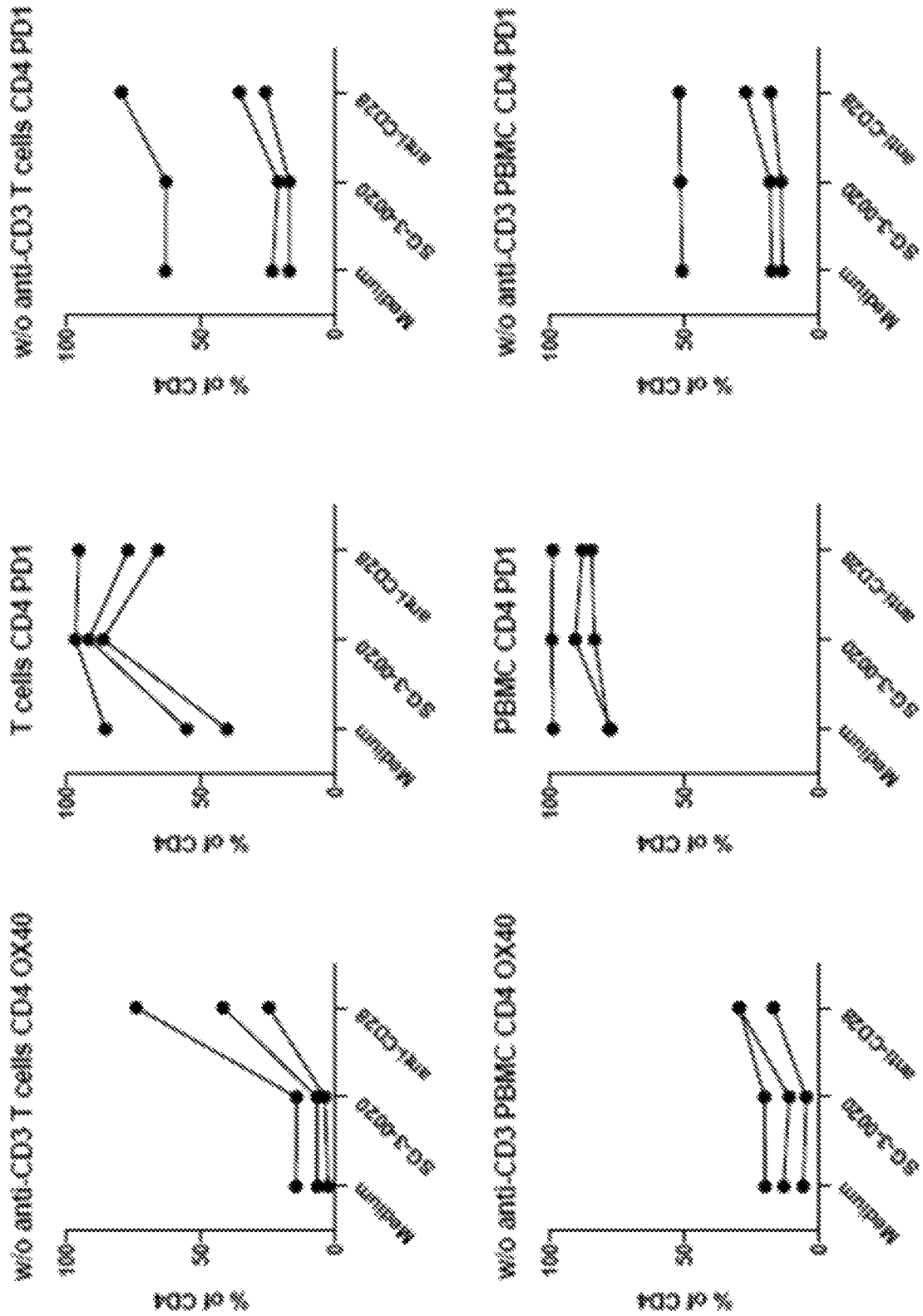
Figure 13C:
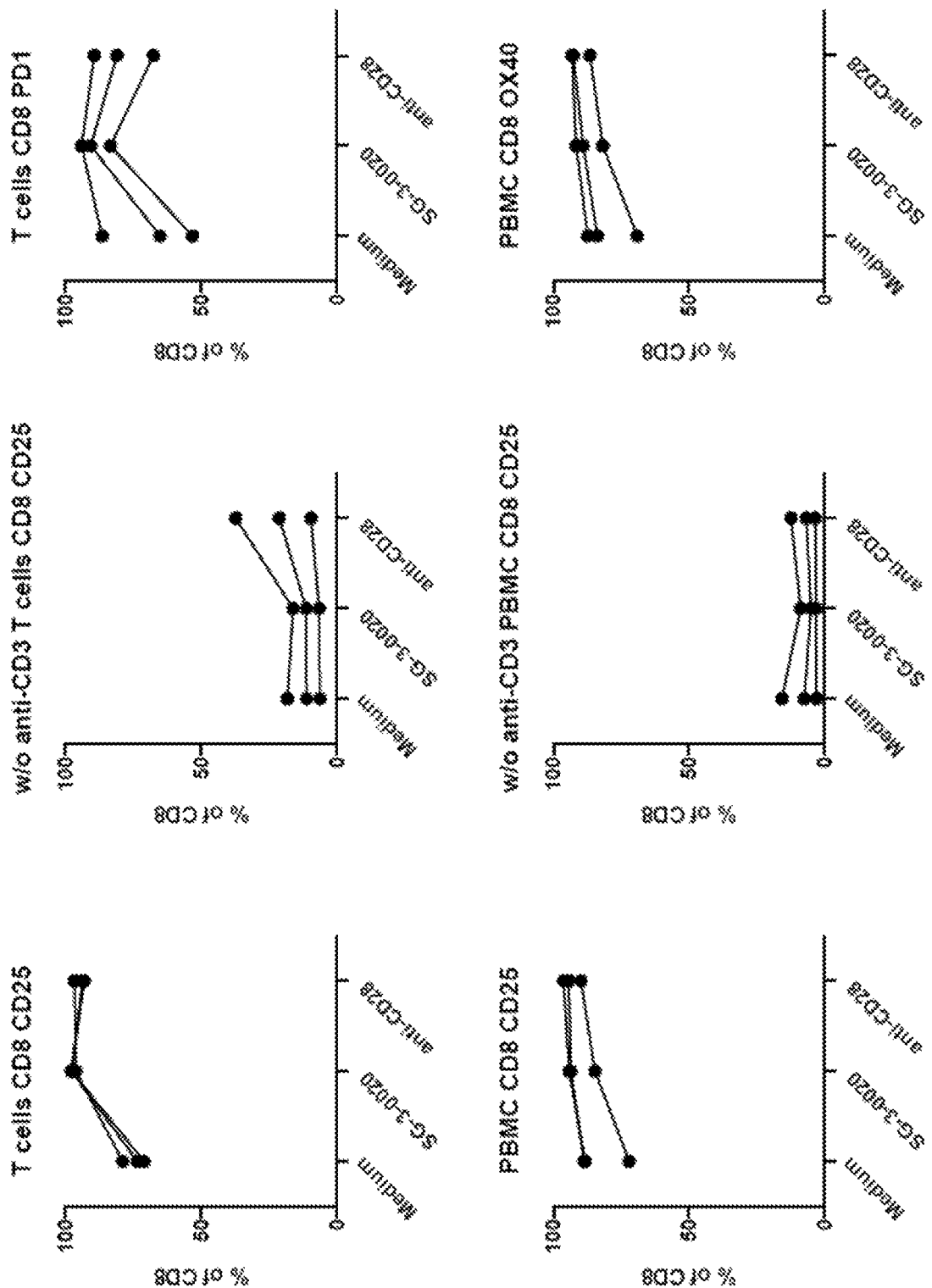
Figure 13D:
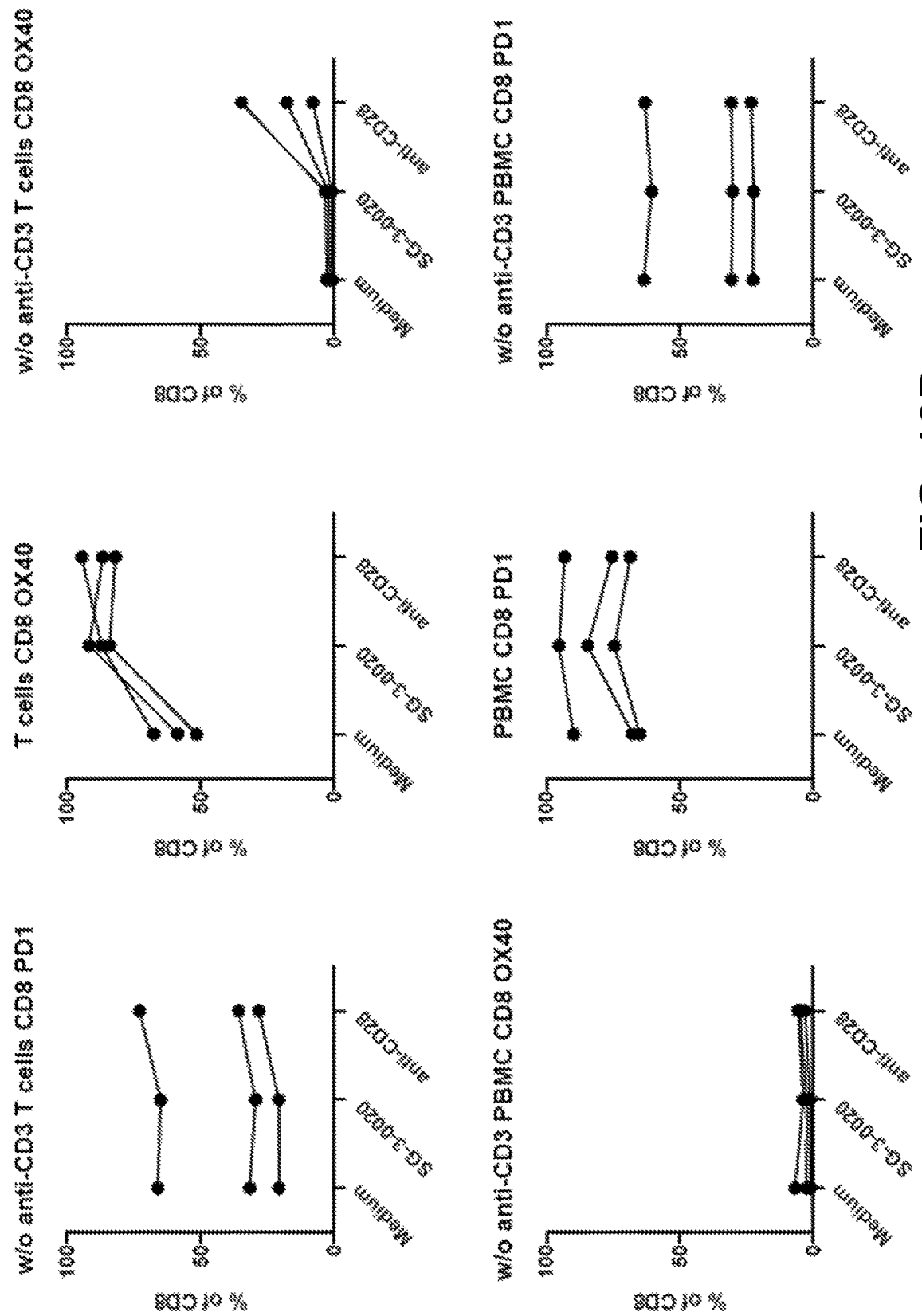

Studies were performed to demonstrate the ability of SG-3-0020 to activate human T cells and to affect adaptive immunity through T cell modulation. PBMCs were obtained from 5 individual human donors. T cells were purified from the frozen PBMCs (Easy Sep™ Human T Cell Isolation Kit (Cat. No. 17951, StemCell Technologies). A summary of the protocol is provided in FIG. 4 In vitro activation of the human T cells was performed according to the protocol provided in FIG. 5A. The protocol used for flow cytometry analysis is provided in FIG. 5B. In summary, purified T cells were incubated with anti-CD3 antibody with SG-3-0020 or with anti-CD28 antibody as a control. The results, provided in FIGS. 6A, 6B, 6C, and 6D, show that incubation of the T cells with SG-3-0020 increased PD-1 expression on both CD4$^+$ and CD8$^+$ cells (FIG. 6A). Furthermore, incubation of the T cells with SG-3-0020 increased secretion of IL-2 and IFN-γ (FIG. 6B). SG-3-0020 demonstrated cytokine-stimulating activity in 5/5 donors in purified T cell system in the presence of anti-CD3 antibody (FIGS. 6C and 6D; FIGS. 12A and 12B). These data demonstrate that SG-3-0020 augments activation of human T cells. Such activation may enhance immune action against a tumor in vivo with or without a co-therapy.

Example 3. Effect of SG-3-0020 on Immune Cell Modulation In Vivo

In vivo studies were performed to study the effects of SG-3-0020 administration on, e.g., immune cell activation and tumor size and to test different routes of administration of SG-3-0020 in CT26 tumor-bearing Balb/c mice and its effects on immune modulation. This mouse model is one of the most widely used mouse models for preclinical testing of new immunotherapeutic drugs (Grosso and Jure-Kunkel, 2013, Cancer Immun, 13:5).

Mice were dosed i.v., i.p., p.t. with SG-3-0020 or PBS. For comparison mice were dosed with CD80-Fc or IgG1-Fc i.v. On Day 7, tumor samples were analyzed for tumor infiltrating lymphocyte (TIL) composition/activation by flow cytometry. The protocol used in this experiment is illustrated in FIG. 7A.

FIG. 7B shows SG-3-0020 TIL immune activation. For example, there was an increase in NK cells, CD8+CD25+ cells, CD8+Ki67+ cells and CD8+OX40+ cells, all indicative of increased activation of immune cells which may combat tumor growth and/or viability.

Tetramer staining (AH1 epitope) was also performed (protocol provided in FIG. 8) and showed SG-3-0020 administration also had a positive effect supporting the therapeutic potential of this protein for immunotherapy of cancer (see FIG. 10).

A similar experiment performed using the CT26 mouse model was performed with preliminary results suggesting that administration of SG-3-0020 as a monotherapy resulted in a decrease in tumor volume (data not shown).

Example 4. Effects of SG-3-0020 on Mouse T Cells 96-well culture plates were pre-coated with anti-CD3 (0.1 mcg/mL) in 200 mcL. The plates were incubated overnight at 4° C. The plates were washed with PBS three times before plating the cells (Balb/c splenocytes for T-cell isolation by EasySep™ #19851). The cells were plated at 100-200K/well in final volume of 200 mcL of AIM-V. Peptides (10mcM) or 2 mcg/mL anti-CD28 were added to the cells. The cells were incubated for 48 hours at 37° C.

Figure 11A:
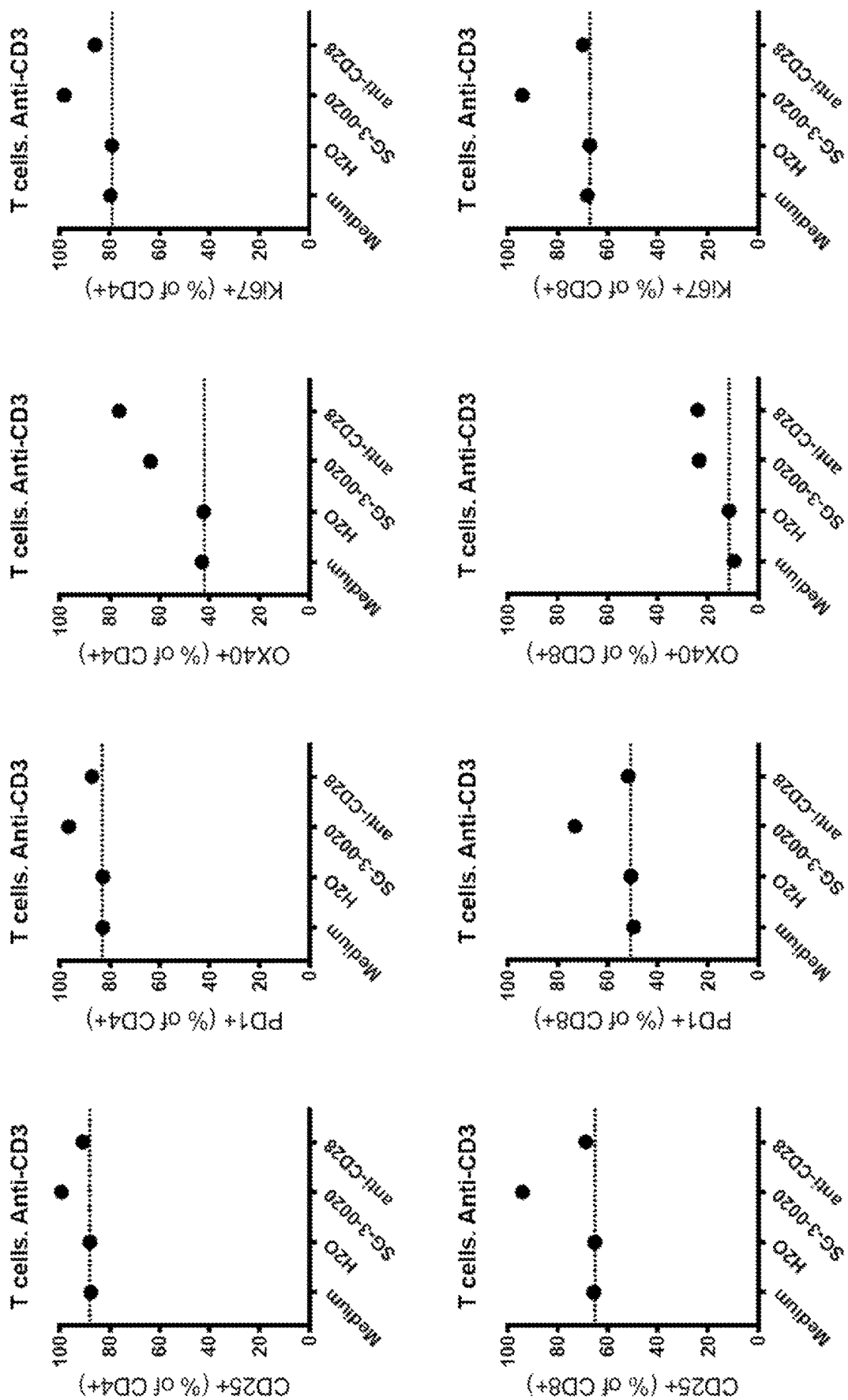
FIGS. 11A and 11B show effects of a therapeutic peptide such as SG-3-0020 on activation of mouse T cells.

The incubated cells were used for flow cytometry analysis. SG-3-0020 increased expression of T cell activation markers and proliferation of CD4 and CD8 T cells isolated from mouse spleens (FIG. 11A).

Figure 11B:
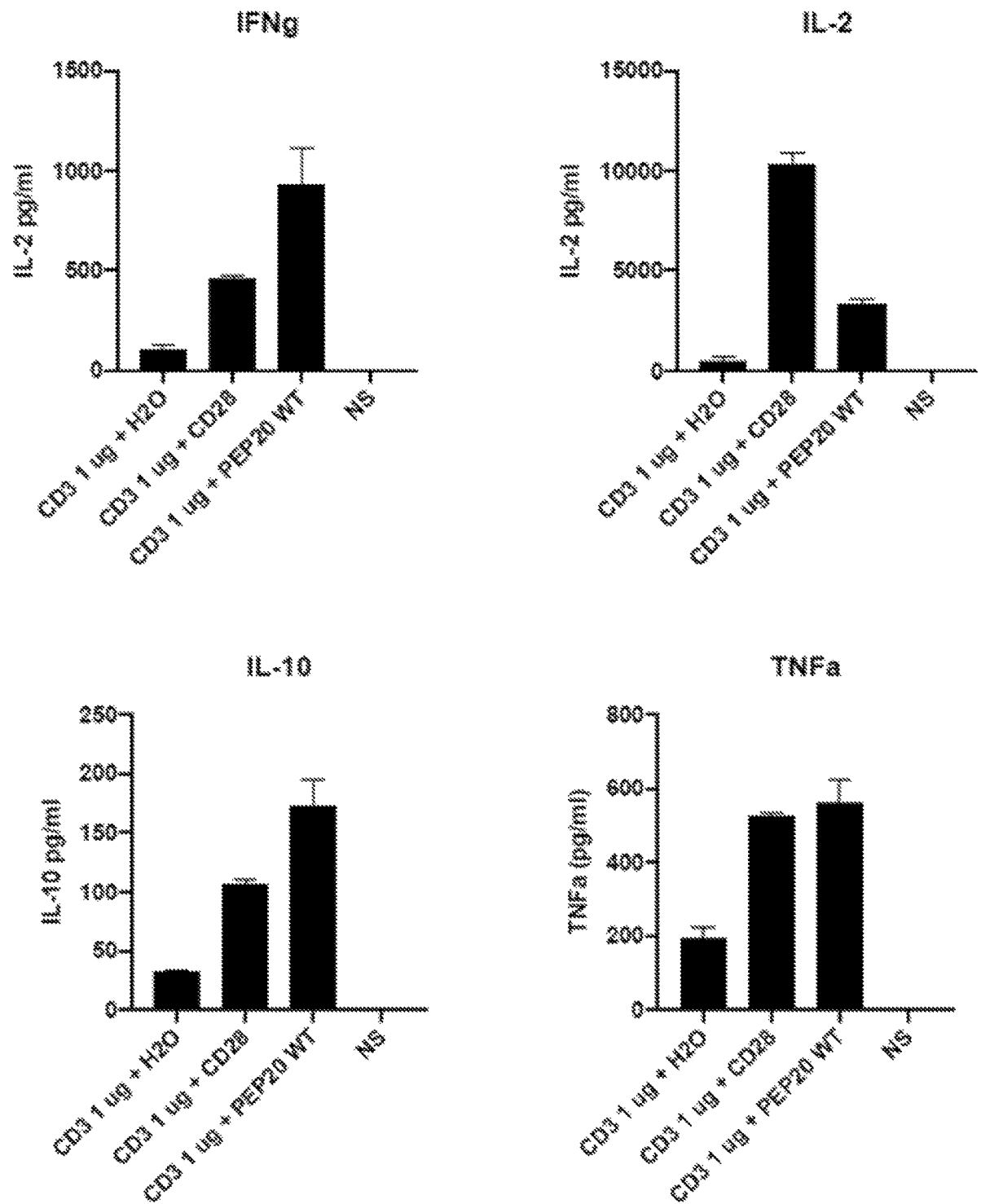

The supernatants were used for MSD analysis. SG-3-0020 increased secretion of effector cytokines by T cells isolated from mouse spleens. (FIG. 11B)

Example 5. Effects of SG-3-0020 on Cells Incubated with an Anti-CD3 Antibody

Activation marker expression on T cells and PBMCs in the presence of peptides (10mcM) or anti-CD28 (10 mcg/mL) was determined after 48 hours of incubation, with or without 0.1 mcg/mL anti-CD3. The data were analyzed by flow cytometry (FIG. 13A-D).

Figure 14:
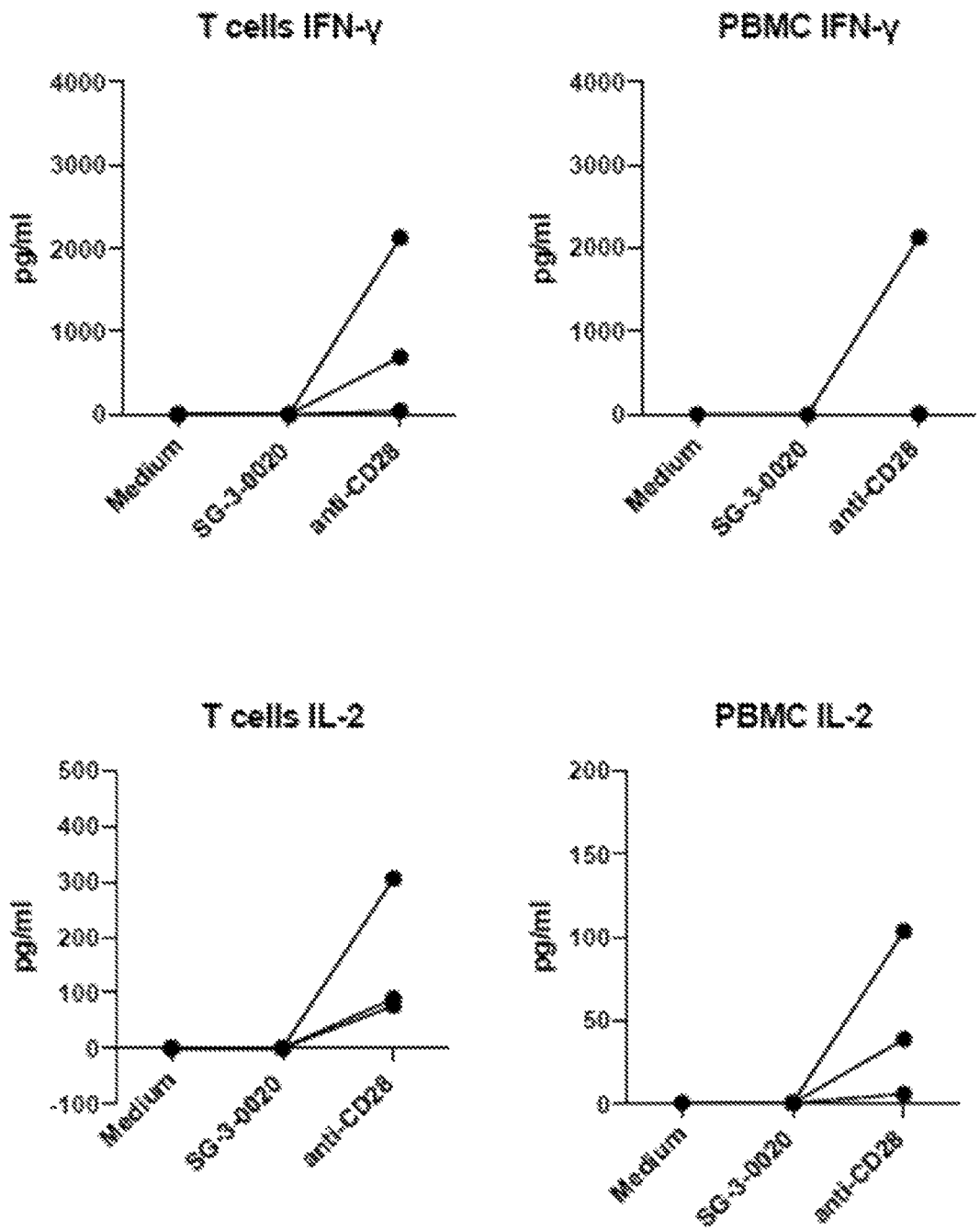
FIG. 14 shows effects of a therapeutic peptide such as SG-3-0020 on CD-3-dependent effector cytokine secretion in human T cells.

Cytokine secretion on T cells in the presence of peptides (10mcM) or anti-CD28 (10 mcg/mL) after 48 h of incubation, with or without 0.1 mcg/mL anti-CD3, was determined. The data were analyzed by MSD (FIG. 14).

Figure 15:
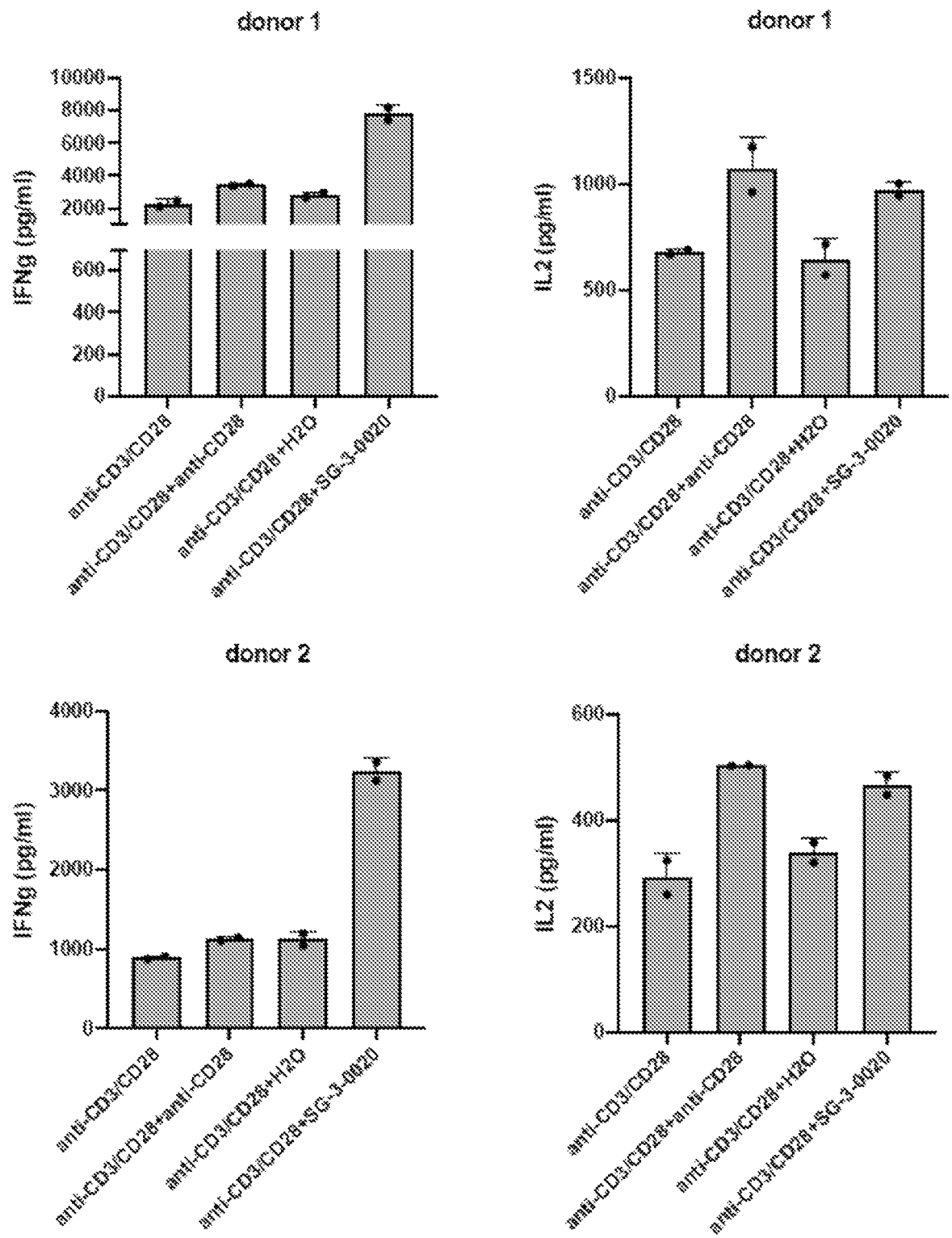
FIG. 15 shows SG-3-0020 increases activity in combination with anti-CD28 activation.

Human T cells were activated with ImmunoCult™ Human CD3/CD28 T Cell Activator in the presence of peptides (10mcM) and cytokine secretion was analyzed after 48 hours of incubation by MSD. SG-3-0020 showed increased activity in combination with anti-CD28 activation (FIG. 15). Activation with anti-CD3 on both isolated T cells and PBMCs was required for SG-3-0020-mediated effects.

Example 6. SG-3-0020 Modulates Expression of Key Immune Genes

Figure 16A:
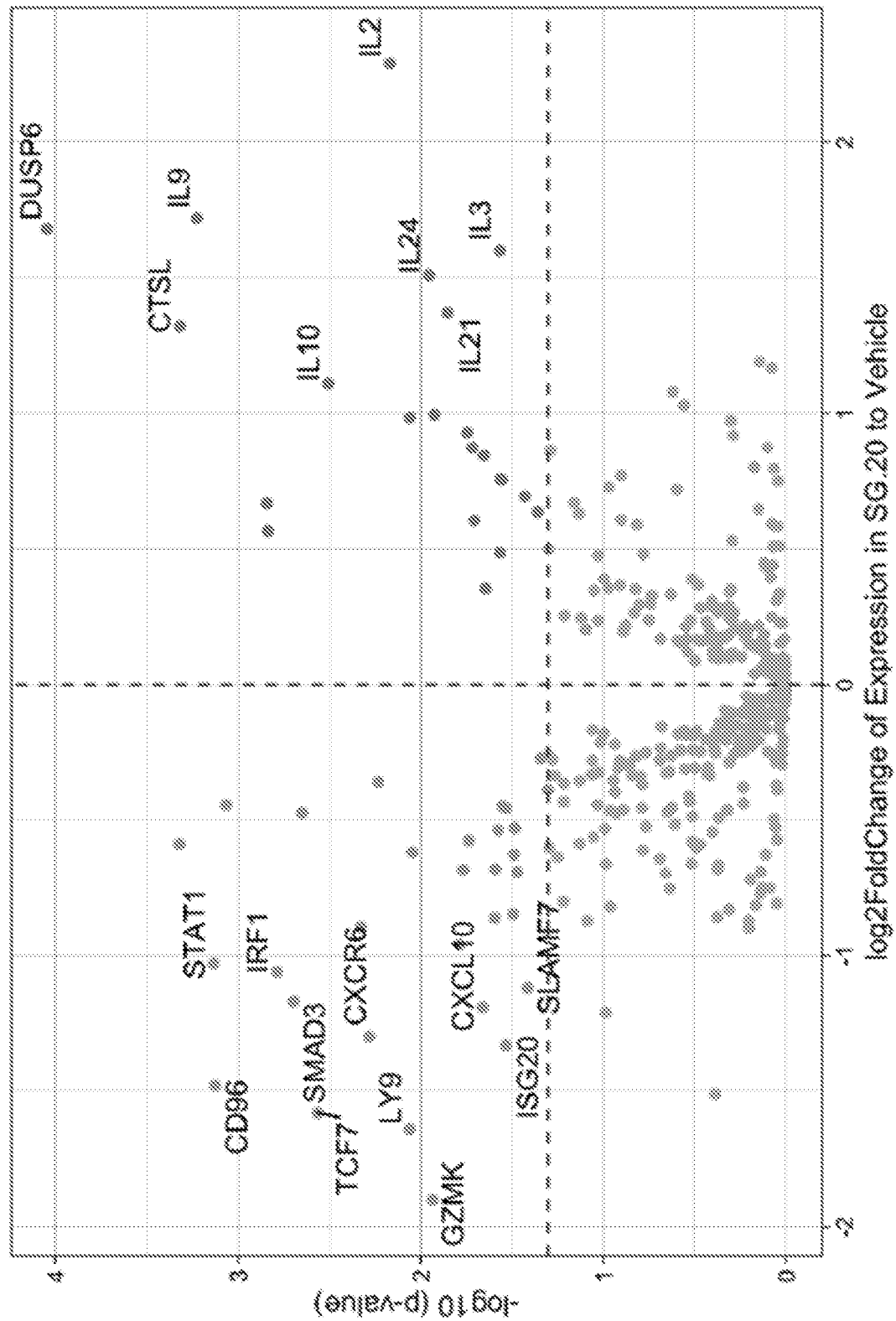
FIGS. 16A and 16B show SG-3-0020 modulates expression of key immune genes by activated human T cell in vitro.
Figure 16B:
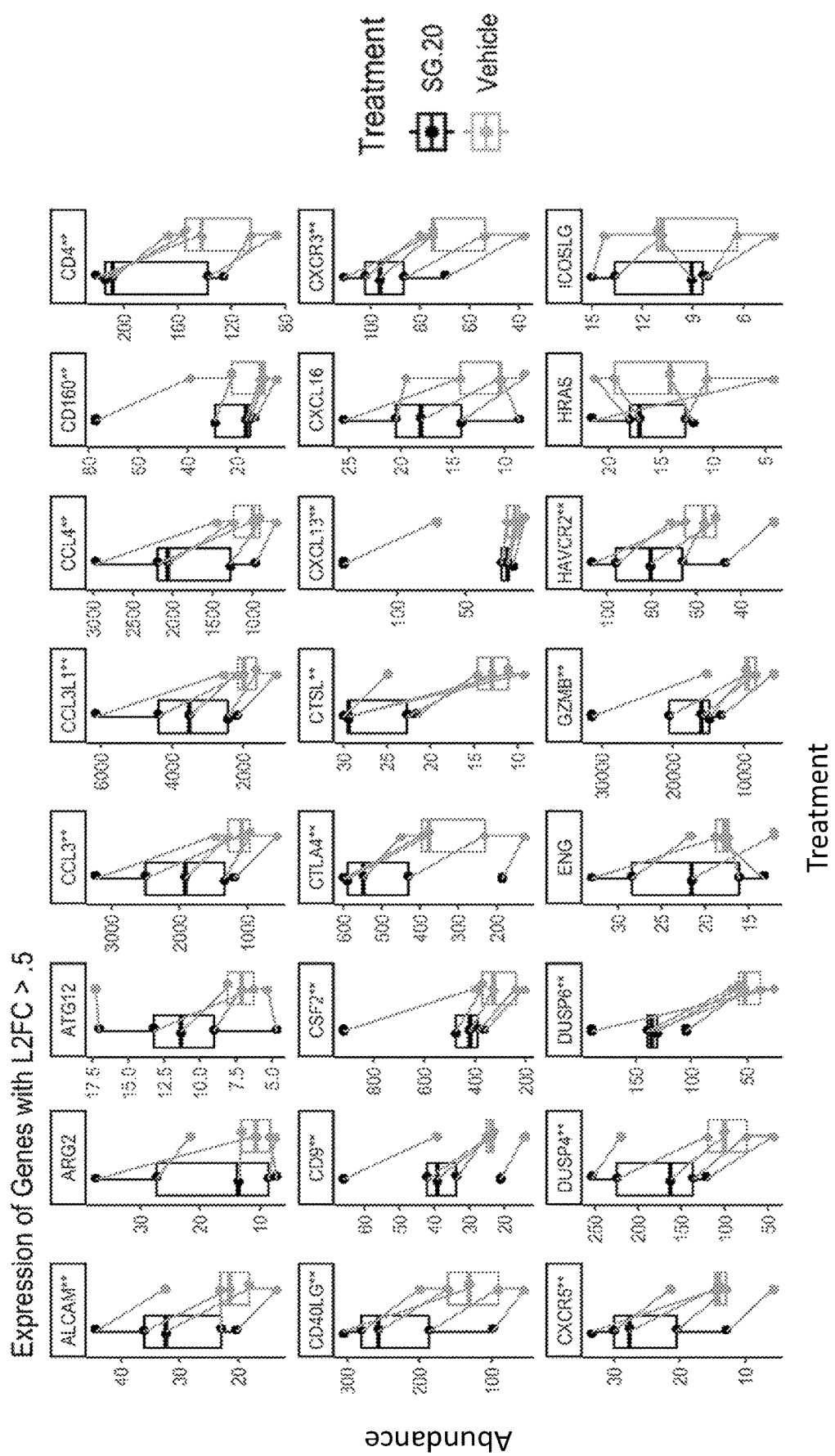
Figure 16B:
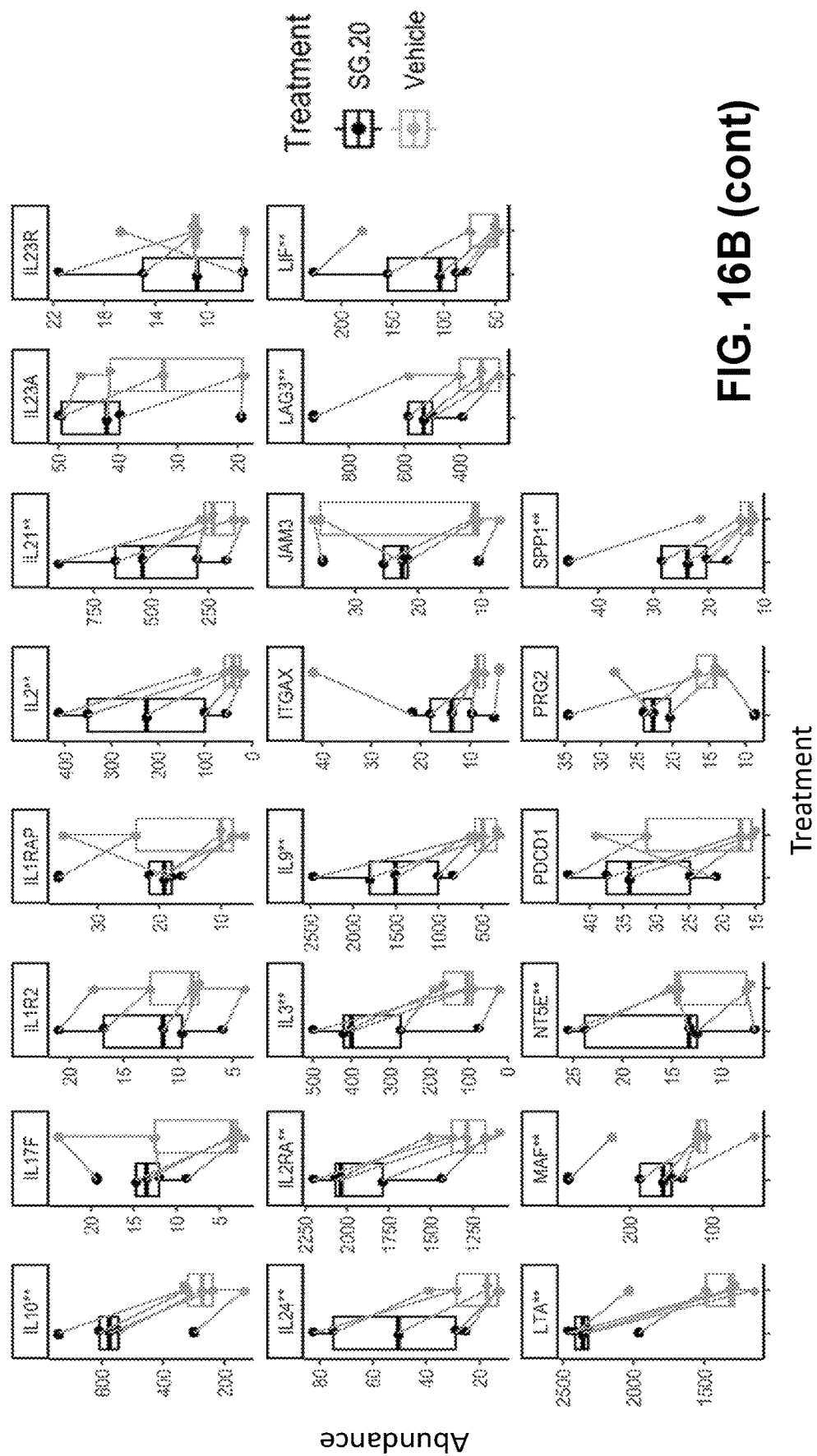

T cells were isolated from 5 individual blood donors and activated as described previously. RNA expression levels were determined by the NanoString nCounter Human Pan-Cancer Immune profiling. Raw data were normalized using built-in positive controls and house-keeping genes (nCounter Expression Data Analysis Guide, NanoString. SG-3-0020 modulated expression of key immune genes by activated human T cell in vitro (FIGS. 16A and 16B). A decrease in expression was observed for signal transducer and activator of transcription 1 (STAT1), interferon regulatory factor 1 (IRF1), cluster of differentiation 96 (CD96), mothers against decapentaplegic homolog 3 (SMAD3), C-X-C motif chemokine receptor 6 (CXCR6), transcription factor 7 (TCF7), lymphocyte antigen 9 (LY9), C-X-C motif chemokine 10 (CXCL10), granzyme K (GZMK), interferon stimulated exonuclease gene 20 (ISG20), and signaling lymphocytic activation molecule F7 (SLAMF7). An increase in expression was observed for dual specificity phosphatase 6 (DUSP6), cathepsin L (CTSL), IL-9, IL-2, IL-10, IL-24, IL-21, and IL-3.

Example 7. SG-3-0020 Binds to Human T Cells

The binding of SG-3-0020 phages to target cells (naïve T-cell, activated T-cell) was tested.

Phage Binding & Biotinylated Peptide Binding

Biotinylated peptide stock (1 mM) was diluted to 1 uM (×1,000-fold) with 1×PBS+2% BSA. 150 mcL of phages (multivalent display) were mixed with 70 mcL of 1×PBS+2% BSA. The solution was rotated at room temperature for 1 hour.

The cells, either naïve T-cells (about $13 \times 10^6$ cells) or activated T-cells (about $16 \times 10^6$ cells) were thawed. The cells were then centrifuged at 1,500 for 5 min at 4° C., and the supernatant was aspirated. The cell pellets were washed with 5 mL of 1×PBS+2% BSA by pipetting. This was repeated such that the pellets were centrifuged and washed a total of 3 times.

The cell pellets were resuspended with 1050 mcL of 1×PBS+2% BSA, and 100 mcL of phage (M13 bacteriophage G8P capsid antibody-FITC from antibodies-online Inc (Cat #: ABIN 125966)) were added into a well of 96-well plates (phage binding). 150 mcL of diluted biotinylated peptide were added into a well of 96-well plates (biotinylated peptide binding). 100 mcL of resuspended cells were added into the wells for phage binding and 50 mcL of resuspended cells were added into the wells for biotinylated peptide binding.

The cells were put on the rocker and incubated at 4° C. for 2 hours for binding and then centrifuged at 1,500 for 5 min at 4° C. The supernatant was discarded. The cell pellets were washed with 250 mcL of 1×PBS+2% BSA by pipetting. The cells were resuspended with 200 mcL of 1×PBS+2% BSA for phage binding and then split for elution and flow cytometry. The cells were resuspended with 100 mcL of 1×PBS+2% BSA for biotinylated peptide binding and centrifuged at 1,500 for 5 min at 4° C.

Elution of Phages

The cells were washed with 250 mcL of 1×PBS for elution. 140 mcL of 7.18 M triethylamine (TEA) were added to 10 mL $H_2O$ to make 0.1 M TEA. Elution was carried out with 100 mcL of freshly prepared 0.1 M TEA. This was immediately neutralized by adding 100 mcL of 1 M TRIS pH 8.0.

Titers of Phages (Input & Elution)

Phages were diluted 10-fold (blocked input & eluted) (10 mcL phage solution+90 mcL of 2×YT). The solutions were diluted 10-fold serially from $10^{-1}$ to $10^{-10}$. 100 mcL ice-chilled TG1 cells were added and incubated for 5 min at room temperature. 10 mcL was taken out from $10^{-5}$ to $10^{-10}$ for input phages and from $10^{-1}$ to $10^{-6}$ for eluted phages. The phages were streaked on 15 cm 2×YT+Carb+2% glucose agar plate and incubated at 30° C. overnight.

Figure 17:
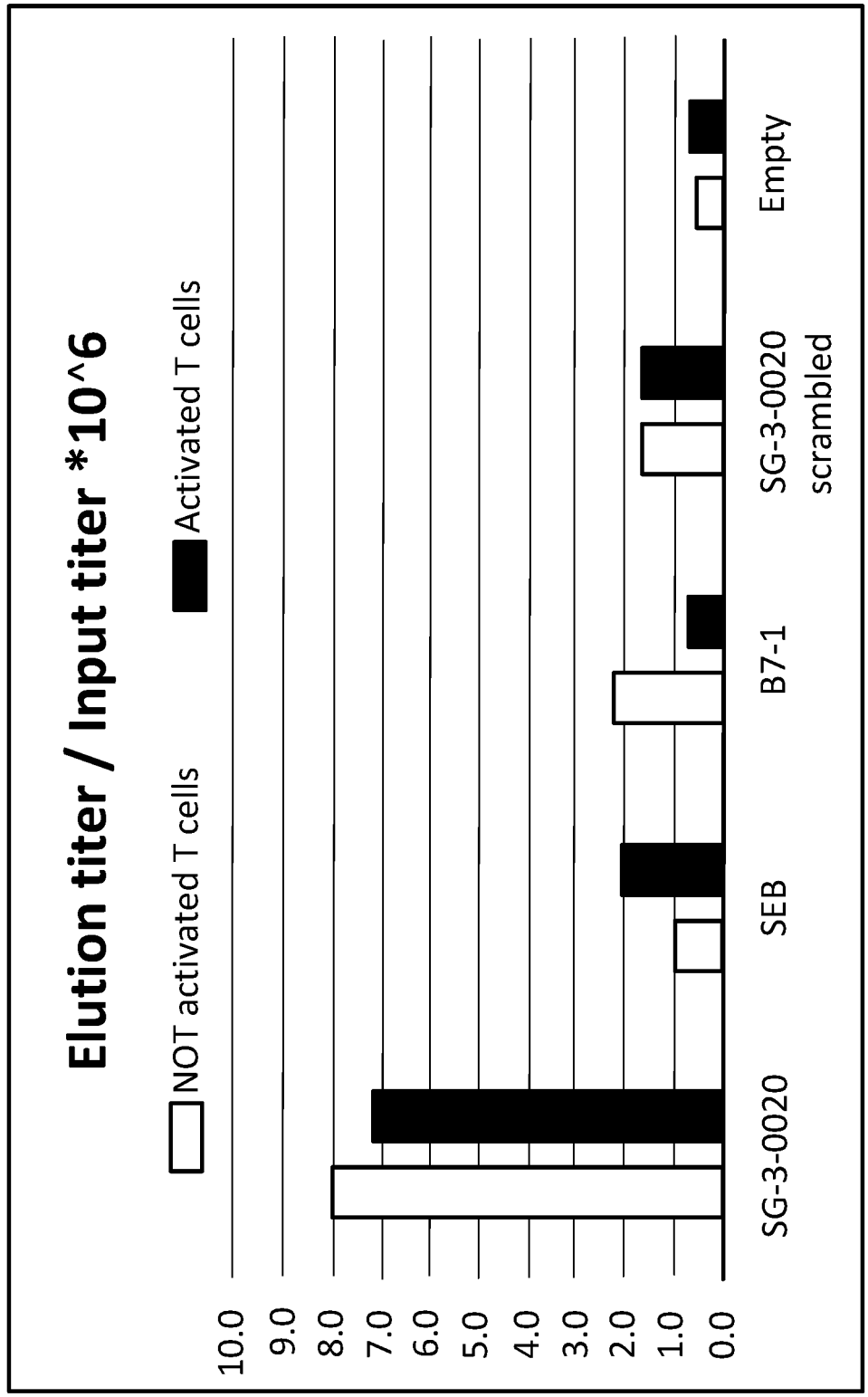
FIG. 17 shows SG-3-0020 binds to human T cells. SEB is a peptide derived from staphylococcal enterotoxin B and is expected to bind to T cells. B7-1 is a peptide derived from the B7-1 protein that could have the potential to bind to T cells. 20-sc is a scrambled version of SG-3-0020 (negative control).

FIG. 17 shows titer results of binding of multivalent display phage encoding for WT SG-3-0020 to not stimulated and anti-CD3 stimulated cells. The titer results also showed SG-3-0020, SEB and SG-3-0020 scrambled were more bound to the activated T-cells compared to empty phages.

Example 9. SG-3-0020 Effect on Intratumoral T Cells

BALB/c male mice (n=5-6/group, 8 weeks of age) were inoculated s.c. with CT26 colon carcinoma cells. SG-B was administered in PBS peritumorally daily at 2.5 mg/kg. Control mice were injected with the corresponding volume of PBS. At Day 13 (AH1 staining)) or Day 7 (Ki67, CD25, OX40 staining) excised tumors were washed with PBS, dissected into smaller fragments using scalpels, and further dissociated into single cell suspensions using the Miltenyi Tumor Dissociation Kit and the GentleMACS Octo dissociator. The digested tumors were filtered through pre-separation filters, washed with PBS, and then used for flow cytometry-based analysis. T lymphocytes were gated as $CD4^+$ or $CD8^+$ and then analyzed for surface marker expression by FlowJo 10.5.3. p values calculated by Mann-Whitney test.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

Sivan, et al. 2015, Commensal *Bifidobacterium* promotes antitumor immunity and facilitates anti-PD-L1 efficacy, Science, Vol. 350, Issue 6264, pgs. 1084-1089.

Needleman et al., 1970, A general method applicable to the search for similarities in the amino acid sequence of two proteins J. Mol. Biol., 48(3): 444-453.

Myers et al., 1988, Optimal alignments in linear space, CABIOS 4: 11-17.

Altschul, et al., 1990, Basic local alignment search tool, J. Mol. Biol. 215: 403-410.

Altschul et al., 1997, Gapped BLAST and PSI-BLAST: a new generation of protein database search programs, Nucleic Acids Res. 25(17): 3389-3402.

Henikoff et al., 1992, Amino acid substitution matrices from protein blocks, Proc. Natl. Acad. Sci. 89(22): 10915-10919.

Karlin et al., 1993, Applications and statistics for multiple high-scoring segments in molecular sequences, Proc. Natl. Acad. Sci. 90: 5873-5877.

Higgins et al., 1988, CLUSTAL: a package for performing multiple sequence alignment on a microcomputer, Gene 73: 237-244.

Pearson et al., 1988, Improved tools for biological sequence comparison, Proc. Natl. Acad. Sci. 85: 2444-2448.

Bowie et al., 1990, Deciphering the message in protein sequences: tolerance to amino acid substitutions, Science 247: 1306-1310.

IUPAC Commission on the Nomenclature of Organic Chemistry (CNOC) and IUPAC-IUB Commission on Biochemical Nomenclature (CBN), 1975, Nomenclature of α-Amino Acids, (Recommendations 1974), Biochemistry 14: 449-462.

Remington's Pharmaceutical Sciences, 17th edition, Alfonso R. Gennaro (Ed.), Mark Publishing Company, Easton, PA, USA, 1985.

Encyclopedia of Pharmaceutical Technology, 3rd edition, James Swarbrick (Ed.), Informa Healthcare USA (Inc.), NY, USA, 2007.

Berge et al., 1977, Pharmaceutical salts, J. Pharm. Sci. 66: 1-19.

Handbook of Pharmaceutical Salts: Properties, Selection, and Use, Stahl and Wermuth, Wiley-VCH, 2002.

In re Bergstrom, 427 F.2d 1394, (CCPA 1970)

In re Bergy, 596 F.2d 952 (CCPA 1979)

Parke Davis & Co. v. H.K. Mulford & Co., 189 F. 95 (S.D.N.Y. 1911) aff'd in part, rev'd in part, 196 F. 496 (2d Cir. 1912)

Merck & Co., Inc., v. Olin Mathieson Chemical Corporation, 253 F.2d 156 (4th Cir. 1958)

Horhota et al., 2006, Glycerol nucleoside triphosphates: Synthesis and polymerase substrate activities, Organic Letters 8: 5345-5347.

Jensen O. N. (2004) Modification-specific proteomics: Characterization of post-translational modifications by mass spectrometry. Curr Opin Chem Biol. 8, 33-41.

Ayoubi T. A. and Van De Ven W. J. (1996) Regulation of gene expression by alternative promoters. FASEB J. 10, 453-60.

Walsh C. (2006) Posttranslational modification of proteins: Expanding nature's inventory. Englewood, Colo.: Roberts and Co. Publishers. xxi, 490 p. p.

Gaston B. M. et al. (2003) S-nitrosylation signaling in cell biology. Mol Interv. 3, 253-63.

Jaffrey S. R. and Snyder S. H. (2001) The biotin switch method for the detection of S-nitrosylated proteins. Sci STKE. 2001, pl1.

Han P. and Chen C. (2008) Detergent-free biotin switch combined with liquid chromatography/tandem mass spectrometry in the analysis of S-nitrosylated proteins. Rapid Commun Mass Spectrom. 22, 1137-45.

Imai S. et al. (2000) Transcriptional silencing and longevity protein SIR2 is an NAD-dependent histone deacetylase. Nature. 403, 795-800.

Glozak M. A. et al. (2005) Acetylation and deacetylation of non-histone proteins. Gene. 363, 15-23.

Yang X. J. and Seto E. (2008) Lysine acetylation: Codified crosstalk with other posttranslational modifications. Mol Cell. 31, 449-61.

Chan et al. "A simple guide to the terminology and application of leucocyte monoclonal antibodies." Histopathology, 1988, Vol. 12, Issue 5, pgs. 461-480.

Engel et al. "CD Nomenclature 205: Human Leukocyte Differentiation Antigen Workshops as a Driving Force in Immunology." J. Immunology, 2015, Volume 195, Issue 10, pgs. 4555-4563.

Sato and Fujita. "Dendritic Cells—Nature and Classification." Allergology International, 2007, Volume 56, Issue 3, pgs. 183-191.

Immunostimulatory nucleic acids and cancer medicament combination therapy for the treatment of cancer (U.S. application Ser. No. 10/668,050, US 2006-0211639 A1).

Roychoudhuri et al. "Interplay of effector and regulatory T cells in cancer." Current Opinion in Immunology, 2015, Volume 33, pgs. 101-111.

American Cancer Society. "Cancer Facts & Figures." 2016 Annual Cancer Facts and Figures, pgs. 1-72.

What is claimed is:

1. A method for treating a disease in a subject in need thereof, comprising:

administering to the subject a pharmaceutical composition, comprising:

i. a therapeutic peptide comprising an amino acid sequence having at least 95% sequence identity to SEQ ID NO:1; and ii. a pharmaceutically acceptable carrier.

2. The method according to claim 1, wherein the peptide comprises an amino acid sequence having at least 99% sequence identity to SEQ ID NO:1.

3. The method according to claim 1, wherein the peptide comprises the amino acid sequence of SEQ ID NO:1.

4. The method according to claim 1, wherein the peptide modulates the production of at least one cytokine in the subject.

5. The method according to claim 1, wherein the peptide modulates the production of at least one cytokine in the subject wherein the cytokine is selected from the group consisting of TNF-α, IL-17, IL-1β, IL-2, IFN-γ, IL-6, IL-12, IL-25, IL-33, IL-8, MCP-1, MIP-3α, CXCL1, IL-23, IL-4, IL-10, IL-13, IFN-α, and TGF-β.

6. The method according to claim 1, wherein the peptide increases Th1 activation, increases dendritic cell maturation, increases CD70 expression, or increases the clonal expansion of $T_{eff}$ in the subject.

7. The method according to claim 1, wherein the pharmaceutical composition is formulated for oral administration.

8. The method according to any claim 1, wherein the disease is a neoplasm.

9. The method according to claim 1, wherein the disease is cancer.

10. The method according to claim 1, wherein the disease is at least one selected from the group consisting of: basal cell carcinoma, biliary tract cancer, bladder cancer, bone cancer, brain and central nervous system cancer, breast cancer, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, small-cell lung cancer, non-small-cell lung cancer, Hodgkin's lymphoma, non-Hodgkins lymphoma, melanoma, myeloma, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, or cancer of the urinary system.

* * * * *